Figure 1A:
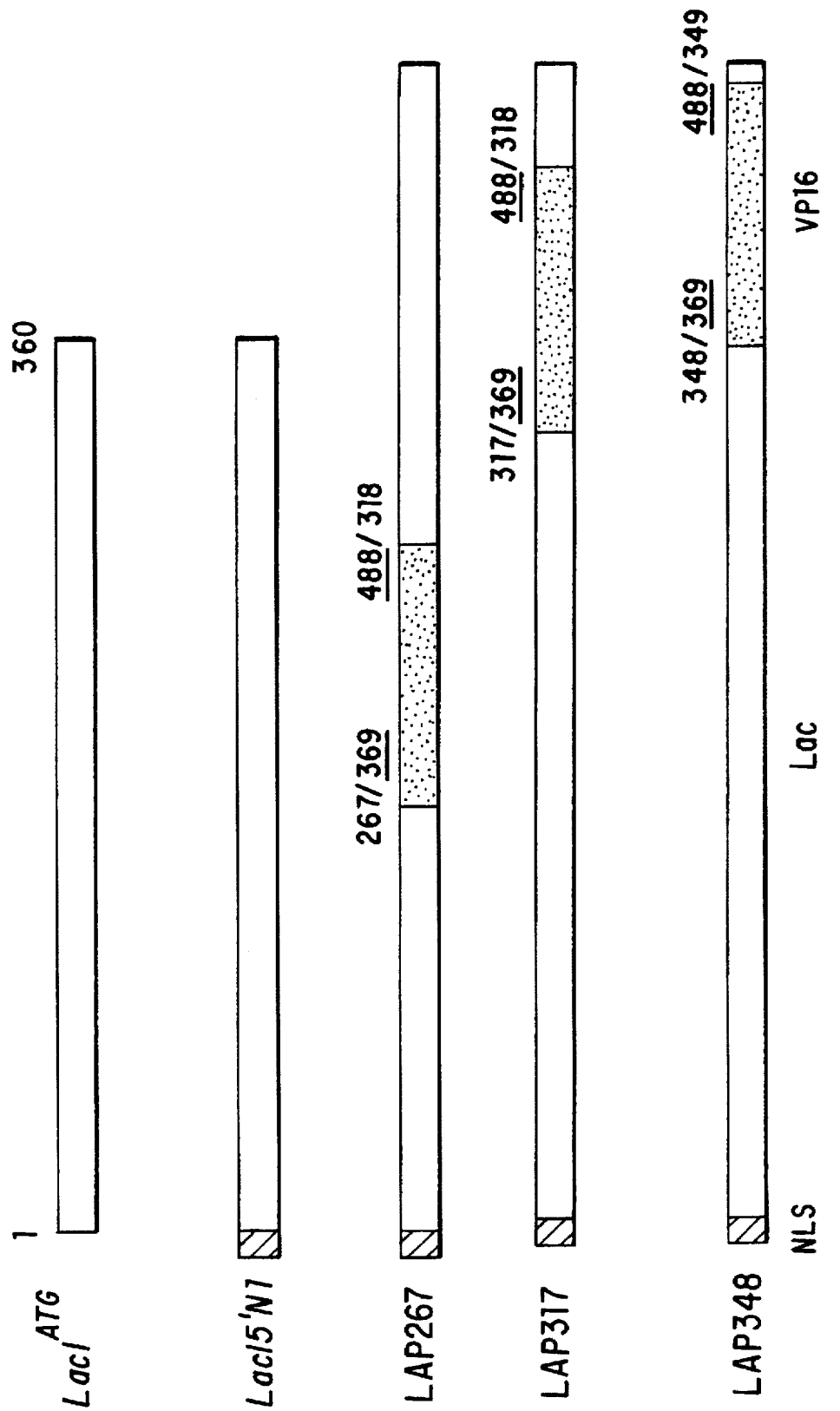

US005674730A

United States Patent [19]
Baim et al.

[11] Patent Number: 5,674,730
[45] Date of Patent: Oct. 7, 1997

[54] EUKARYOTIC CELLS COMPRISING A DNA SEQUENCE ENCODING A BACTERIAL-VIRAL CHIMERIC TRANSACTIVATOR PROTEIN

[75] Inventors: Steven B. Baim; Mark A. Labow; Thomas E. Shenk; Arnold J. Levine, all of Princeton, N.J.

[73] Assignee: The Trustees of Princeton University, Princeton, N.J.

[21] Appl. No.: 41,297

[22] Filed: Mar. 30, 1993

Related U.S. Application Data

[62] Division of Ser. No. 537,404, Jun. 13, 1990, abandoned.

[51] Int. Cl.[6] .............................. C12N 5/00; C12N 15/00; C07H 21/04
[52] U.S. Cl. .................................. 435/240.2; 435/240.2; 435/320.1; 536/23.4
[58] Field of Search ..................... 536/23.1; 435/240.2, 435/320.1

[56] References Cited

PUBLICATIONS

Sadowski et al (1988) Nature 335, 563–564.
Hu et al (1987) Cell 48, 555–566.
Lanford et al (1986) Cell 46, 575–582.
Khillan et al. 1988 Nucleic Acids Res 16, 1423–1430.
Deuschle et al., 1989, PNAS 86:5400–5404.
Fuerst et al., 1989, PNAS 86:2549–2553.
Figge et al., 1988, Cell 52:713–722.
Preston, 1988, Cell 52:425–434.
Smith et al., 1988, EMBO J. 7:3975–3982.
Triezenberg, 1988, Genes & Dev. 3:718–729.
Brown et al., 1987, Cell 49:603–612.
McKnight et al., 1987, PNAS 84:7061–7065.
Brent et al., 1985, Nature 312:612–615.
Simons et al., 1984, PNAS 81:1624–1628.
Chao et al., 1980, Biochem. 19:3254–3260.
Cousens et al., 1989 "The C-Terminal 79 Amino Acids of the Herpes Simplex Regulatory Protein, VMW65, Efficiently Activate Transcription in Yeast and Mammalian Cells in Chimeric DNA–Binding Proteins", EMBO J. 8:2337–2342.
Kalderon et al., 1984, "A Short Amino Acid Sequence Able to Specify Nuclear Location", Cell 39:499–509.
Kalderon et al., 1984, "Sequence requirements for nuclear location of simian virus 40 large–T antigen", Nature 311:33–38.
Freshney, 1983, "Culture of Animal Cells: A Manual of Basic Techniques", Alan R. Liss, Inc. pp. 104–118.

*Primary Examiner*—Jacqueline M. Stone
*Assistant Examiner*—Deborah Crouch
*Attorney, Agent, or Firm*—Pennie & Edmonds

[57] ABSTRACT

The present invention relates to novel chimeric transactivating proteins comprising a functional portion of a DNA binding protein and a functional portion of a transcriptional activator protein. The chimeric transactivating proteins of the invention offer a variety of advantages, including the specific activation of expression of genes engineered to comprise transactivator responsive elements, thereby achieving exceptionally high levels of gene expression. Furthermore, in various embodiments of the invention, the transactivator proteins may be used to increase expression of some genes while repressing the expression of others, thus permitting a greater degree of control of gene expression patterns than other currently available systems. In preferred embodiments of the invention, the function of the chimeric transactivator proteins may be induced, for example, by chemical agents (e.g. IPTG) or changes in temperature. In a preferred specific embodiment of the invention, the ability to switch transactivator function on and off may be utilized in the context of transgenic animals and to develop cell lines capable of differentiation.

11 Claims, 11 Drawing Sheets

|  | RELATIVE ACTIVITY | |
|---|---|---|
|  | − | LAP 348 |
| SV2 | 1 | 0.5 |
| SVE− | <0.02 | <0.02 |
| L1 | <0.02 | 0.2 |
| L2 | <0.02 | 0.11 |
| L1-1 | <0.02 | 2.1 |
| L1-2 | <0.02 | 3.3 |
| L1-3 | <0.02 | 1.7 |
| L7 | <0.02 | 7.5 |
| L14 | <.02 | >15 |
| ICP0 | 0.15 | 0.17 |
| ICP0/L1 | 0.22 | 2.7 |

FIG. 3

| CAT Plasmid | Promoter Structure | Relative Activity Cotransfected Plasmid | | |
|---|---|---|---|---|
| | | pBR322 | lacI5'NI | LAP348 |
| pX-8 | | 1 | 0.74 ± 0.14 | 0.6 ± 0.15 |
| pSV Lp1 | | 1 | 0.04 ± 0.02 | 0.12 ± 0.05 |
| pSV Lp2 | | 1 | 0.31 ± 0.06 | 2.2 ± 0.06 |
| pSV Lp3 | | 1 | 0.66 ± 0.16 | 4.5 ± 0.7 |
| pSV Lp1-3 | | 1 | 0.07 ± 0.01 | 0.15 ± 0.01 |

FIG. 5

| Cell | Marker | Number of Colonies | | |
|---|---|---|---|---|
| | | − | LAP348 | LAP+clones |
| HeLa | L1-3neo | 3 | 40 | 6/6 |
| Ltk | L1-3neo | >200 | 75 | 1/7 |
| REF | L2 T-antigen | 0,0 | 31, 34 | 5/6 |

EUKARYOTIC CELLS COMPRISING A DNA SEQUENCE ENCODING A BACTERIAL-VIRAL CHIMERIC TRANSACTIVATOR PROTEIN

This is a division of application Ser. No. 07/537,404, filed Jun. 13, 1990, now abandoned.

1. INTRODUCTION

The present invention relates to novel chimeric transactivating proteins comprising portions of DNA binding proteins as well as transcriptional activating proteins which can function in vertebrate cells. In particular embodiments of the invention, fusion proteins between the bacterial lacI DNA binding protein and the activation domain of the mammalian Herpes simplex virus VP16 protein may be used as isopropyl β-D-thiogalactoside (IPTG) regulatable transactivators of promoters linked to lac operator sequences. The novel vertebrate transcriptional transactivator proteins of the invention may be used to selectively induce high levels of expression of genes engineered to include transactivator responsive elements.

2. BACKGROUND OF THE INVENTION

Widespread research efforts have been directed toward elucidating the molecular mechanisms of gene expression. The motivation for this research lies, in part, in a desire to understand the basis for selective expression of genes in differentiated cells, and also in an attempt to acquire the ability to control and manipulate the expression of genes of interest.

Inducible gene expression systems have been key tools in elucidating the function of a wide variety of genes in bacteria, yeast and Drosophila. It is only recently that similar systems for vertebrate cells have been characterized. These systems are of two types. First, transcriptional promoters responsive to various treatments such as heat shock, heavy metals or hormones have been used (e.g. Brinster et al. 1982, Nature 296:39–42; Hynes et al. 1981, Proc. Natl. Acad. Sci. USA 78:2038–2042; Searle et al. 1985, Mol. Cell Biol. 5:1490–1489; Israel and Kaufman, 1989, Nuc. Acids Res. 17:4589–4604). The main advantage to these systems is that expression can be induced more than 100-fold in some cases. However, these systems have several inherent disadvantages. Because the promoters are responsive to normal cellular transactivators, induction presumably alters the expression of many endogenous genes in addition to the gene being studied. These promoters often have relatively high basal activities and variable induced levels (Hynes et al. 1981, Proc. Natl. Acad. Sci. USA 78:2038–2042; Brinster et al. 1982, Nature 296:39–42;). Further, induction with hormone and heat shock have pleiotropic effects on cell physiology in addition to their effect on transcription (Firestone et al. 1982, Nature 300:221225; Lee et al. 1988, Proc. Natl. Acad. Sci. USA 85:1204–1208).

A second approach utilizes bacterial repressor proteins of *Escherichia coli* to repress transcription in mammalian cells. In bacteria, such proteins are used to reversibly bind to operator sequences controlling the expression of non-constitutive genes. Under the appropriate circumstances, binding of the repressor protein is released, permitting expression of the non-constitutive gene. This system of gene control increases the efficiency of bacterial cell function by curtailing gratuitous expression of genes which are only used under certain particular circumstances. These bacterial repressor proteins offer a distinct advantage as regulatory switches in that the recognition sequences (the operators) for the repressor are relatively unique to the gene being studied. Both the lex and lac repressors have been used in mammalian cells (Brown et al. 1987, Cell 49:603–612; Hu and Davidson 1987, Cell 48:555–566; Smith et al. 1988, EMBO 7:3975–3982). The lac repressor is particularly useful in that its DNA binding activity is strongly inhibited by IPTG. Several groups have shown that the lac repressor can inhibit expression of eukaryotic viral promoters containing operators downstream of the TATA box, downstream from a vaccinia virus promoter, or from an SV40 promoter in mammalian cells and that repression can be largely relieved with IPTG (Brown et al. 1987, Cell 49:603–612; Hu and Davidson 1987, Cell 48:555–566; Figge et al. 1988, Cell 52:713–722; Deuschle et al. 1989, Proc. Natl. Acad. Sci. USA 86:5400–5404; Fuerst et al. 1989, Proc. Natl. Acad. Sci. USA 86:2549–2553). Unfortunately, repression is generally not complete and it is unclear if high levels of induced expression can be obtained with these vectors.

Eukaryotic transcription factors are often composed of separate and independent DNA binding and transcriptional activator domains (Mitchell and Tjian 1989, Science 245:371–378). The independence of the domains has allowed for the creation of functional fusion proteins consisting of the DNA binding and activating domains of heterologous proteins. Chimeric eukaryotic regulatory proteins, consisting of the lexA DNA binding protein and the activation domain of the yeast transcription factor, Gal4, were constructed by Brent and Ptashne (1985, Nature 312:612–615). The use of fusion proteins has identified several types of protein domains which act as transcriptional activators. These domains have little amino acid similarity but often are characterized as being either highly acidic (as in the case of Gal4), glutamine-rich (as in the case of Sp1), or proline-rich (as in the case of NF1, Ma and Ptashne, 1987, Cell 51:113–119; Courey and Tjian 1988; Mermod et al. 1989, Cell 58:741–753).

One of the most efficient activator domains known is contained in the carboxyl-terminal 100 amino acids of the Herpes Simplex Virus (HSV) virion protein 16 (VP16; Sadowski et al. 1988, Nature 335:563–564; Triezenberg et al. 1988, Genes & Dev. 2:718–729). VP16, also known as Vmw65 or α-gene trans-inducing factor, is a structural protein of HSV which activates transcription of the immediate early promoters of the virus, including those for ICP0 and ICP4 (Campbell et al. 1984, J. Mol. Biol. 180:1–19; Kristie and Roizman 1984, Proc. Natl. Acad. Sci. USA 81:4065–4069; Pellet et al. 1985, Proc. Natl. Acad. Sci. 82:5870–5874). Although VP16 specifically activates promoters containing the so called TAATGARAT element, the specificity is endowed by a cellular DNA binding protein(s) which is complexed with the amino terminal domains(s) of VP16 (McKnight et al. 1987, Proc. Natl. Acad. Sci. USA 84:7061–7065; Preston et al. 1988, Cell 52:425–434).

The lacI repressor, the product of the bacterial lacI gene, has been well characterized. The binding affinity and sequence specificity of lacI protein appears to be extremely high. The $K_d$ of lac for its operator sequence ($10^{-13}$ M) has been asserted to be approximately three orders of magnitude greater than that of the lexA repressor for its operator (Riggs et al. 1970a, J. Mol. Biol. 48:67–83; Brent and Ptashne 1984, Cell 43:729–736). The lac repressor appears to recognize a relatively large, complex, 25 bp operator (Miller 1978, In The Operon. J. H. Miller and W. S. Reznikoff III, eds. (Cold Spring Harbor, N.Y., Cold Spring Harbor Laboratory)). Estimates indicate that as few as three fortuitous lac operator sequences exist in the mouse genome (Simons et al. 1984, Proc. Natl. Acad. Sci. USA 81:1624–1628) suggesting that very few cellular sequences should be recognized by the lacI DNA binding domain. Further, lacI has been observed to function in mammalian cells indicating that lacI can interact with DNA in the context of mammalian chromatin. In fact, packaging of operator-containing DNA by histone octamers has been reported to lower the nonspecific binding of DNA by lac repressor without affecting its specific DNA-binding properties (Chao et al., 1980, Biochemistry 19:3254–3260).

3. SUMMARY OF THE INVENTION

The present invention relates to novel chimeric transactivating proteins comprising a functional portion of a DNA binding protein and a functional portion of a transcriptional activator protein. It is based, in part, on the discovery that a novel mammalian regulatory system was created when the *Escherichia coli lac* repressor was converted into a mammalian transactivator by fusing a nuclear localization signal onto the 5' end of the lacI gene and by inserting the activating region of Herpes Simplex virus type 1 (HSV) VP16 activator protein within the carboxyl terminal region of the lacI gene. The resulting lac activator (LAP) fusion proteins were found to be potent activators of several promoters comprising one or more lac operator sequences, either upstream or downstream, of a gene of interest. Furthermore, LAP was found to be bifunctional, also acting as a repressor of expression of an SV40 promoter/enhancer containing an operator immediately downstream of the SV40 TATA box, and activation could be strongly inhibited by isopropyl β-D-thiogalactoside (IPTG) indicating that LAP retained the functions needed for allosteric regulation. Finally, it was possible to generate a LAP construct that, due to the position of the VP16 sequence insert, was temperature sensitive for activation of target genes carrying lac operator sequences. This LAP protein was reverse-regulated by in that IPTG was able to convert the LAP construct from an inactive to an active state at its normal restrictive temperature.

The chimeric transactivating proteins of the invention offer a variety of advantages, including the specific activation of expression of genes engineered to comprise transactivator responsive elements, thereby achieving exceptionally high levels of gene expression. Furthermore, in various embodiments of the invention, the transactivator proteins may be used to increase expression of some genes while repressing the expression of others, thus permitting a greater degree of control of gene expression patterns than other currently available systems. In preferred embodiments of the invention, the function of the chimeric transactivator proteins may be induced, for example, by chemical agents (e.g. IPTG) or changes in temperature. In a preferred specific embodiment of the invention, the ability to switch transactivator function on and off may be utilized in the context of transgenic animals and to develop cell lines capable of differentiation in culture.

4. DESCRIPTION OF THE FIGURES

FIGS. 1(A–C) Structure and characterization of lac and LAP genes.

(A) Structure of the lacI and representative modified lacI genes. The amino acid coding region of various lacI constructs are shown. The first and last amino acids (1–360) of the wild type lac repressor are shown above the lacI gene. The nuclear localization signal (NLS) and the ATG start codon added to create lacI 5'N1 and LAP genes are depicted by hatched boxes. The location of the VP16 coding region is indicated by stippled boxes. The amino acids of lac repressor at the junctions of the lac and VP16 coding regions and the amino acids of VP16 added (underlined) are indicated above the box (Pellet et al. 1985, Proc. Natl. Acad. Sci. 82:5870–5874). The amino acid numbers given for lac repressor refer to that of the wild type allele (Miller 1978, In The Operon. J. H. Miller and W. S. Reznikoff III, eds. (Cold Spring Harbor, N.Y., Cold Spring Harbor Laboratory)). The amino acids indicated for VP16 do not include 10 amino acids encoded by the vector polylinker.

(B) Immunoprecipitation analysis of lac repressor and LAP proteins. $^{35}$S-methionine labeled proteins from HeLa cells transfected with plasmid DNA encoding several of the lacI genes described above, namely pHCMV lacI$^{ATG}$(lanes 1, 2), pHCMV lacI 5'N1 (lanes 3, 4), pHCMV LAP 317 (lanes 5, 6), or pHCMV LAP 348 (lanes 7, 8) and pAd5VAI/II, were immunoprecipitated with either rabbit preimmune (P) or anti-lac repressor immune serum (I) and analyzed by electrophoresis on a 10% SDS-polyacrylamide gel. All genes were under control of the CMV promoter as described in the text. The size and position of molecular weight standards are shown on the left and the position of the various lac derivative proteins are shown on the right.

The intracellular location of lacI derivatives was determined by indirect immunofluorescence. Here, the fluorescent micrographs of cells transfected with either lacI$^{ATG}$, lacI5'NI or LAP348 are compared.

FIG. 2(A–B) Transactivation of operator-containing promoters by LAPs.

(A) Transactivation of pL1-2CAT by LAP317 and LAP 348. HeLa cells were transfected with 2 μg of either pSV2CAT or pL1-2CAT and 1 μg of pBR322 or lac derivatives as indicated. The total amount of DNA in each transfection was adjusted to 25 μg with carrier calf thymus DNA. Cell extracts were made 48 hours post-transfection and CAT assays carried out as described in the text.

(B) Operator-dependent activation by LAP348. HeLa cells were transfected with 1 μg of either pSV2CAT (lanes 1, 2), pSV$^{Lp3}$CAT (a derivative of SV2CAT containing an operator at position 3 between the enhancer and 21 base pair repeats; lanes 3, 4) or enhancerless SV40 promoter CAT vectors containing 0 (pSVE-CAT; lanes 5, 6), 1 (pL1CAT; lanes 7, 8), 2 (pL1-1CAT; lanes 9, 10), or 3 (pL1-2CAT; lanes 11, 12) operators with pBR322 (−) or with 1 μg of pHCMV-LAP348 (+) as indicated. Transfections and CAT assays were carried out as described in FIG. 2(A).

FIG. 3 Structure and transactivation of various promoters by LAP348. The structures of the SV40 promoter constructs are shown in detail. The promoters and designations for the CAT constructs are shown on the left. The two SV40 72-base pair enhancers are represented as hatched boxes, the 21 base pair repeats containing the SV40 Sp1 binding sites as open boxes, the TATA box and origin of DNA replication as a circle and the start site of transcription as an arrow. Operators are indicated by stippled boxes. The long arrows represent tandem copies of operators present in either pL1-2CAT (A) or pL1-3CAT (B). Dotted lines represent vector sequences. The ICP0 promoter is indicated separately as a long grey box. HeLa cells were transfected and CAT assays performed as described above and in the text. The relative activities of the various constructs are expressed as the fraction of activity compared to that produced after transfection with pSV2CAT alone. The numbers reported in this figure represent the averages from between 3 to 5 independent transfection experiments and include standard deviations.

FIG. 4 LAP348 increases levels of reporter RNA. Cells were transfected with carrier DNA only (Barany, 1985, Gene 37:111–123) or with pL1-3neo (Besse et al., 1986, EMBO 5:1377–1381), pL1-3neo and pHCMVLAP348 (Beyreuther, 1978, In The Operon. J. H. Miller and W. S. Reznikoff III, eds. (Cold Spring Harbor, N.Y., Cold Spring Harbor Laboratory) or pHCMVLAP348 (Boshart, et al., 1985, Cell 41:521–530). Cytoplasmic RNAs were prepared and analyzed by RNase protection as described in Experimental Procedures. The robe used in A was a 360 base antisense neo probe (Jones and Cole, 1987, Mol. Cell. Biol. 7:4513–4521) and in B was an antisense human β-actin probe (a gift of L. S. Chang, Princeton University). 20 μg of RNA and 2 μg of RNA were used in A and B, respectively. The size of molecular weight markers in nucleotides (1 kb ladder; Bethesda Research Lab) is shown on the left (M) and the unreacted probe is shown in lane P. Panel A is a two day exposure and panel B is a 4 hour exposure.

FIG. 5 Position dependent activation and repression by LAP348. HeLa cells were transfected with 2 μg of the indicated CAT reporter construct and PBR322 or with either 5 μg of either the pHCMV lacI5'N1 (LacI) or pHCMV-LAP348 constructs as indicated. The structure of the various SV40 promoters are indicated as described in FIG. 3. The relative activities shown are normalized to the transfection with carrier DNA and BR322. The numbers shown are averages from three independent experiments and include the standard deviations.

Figure 6:
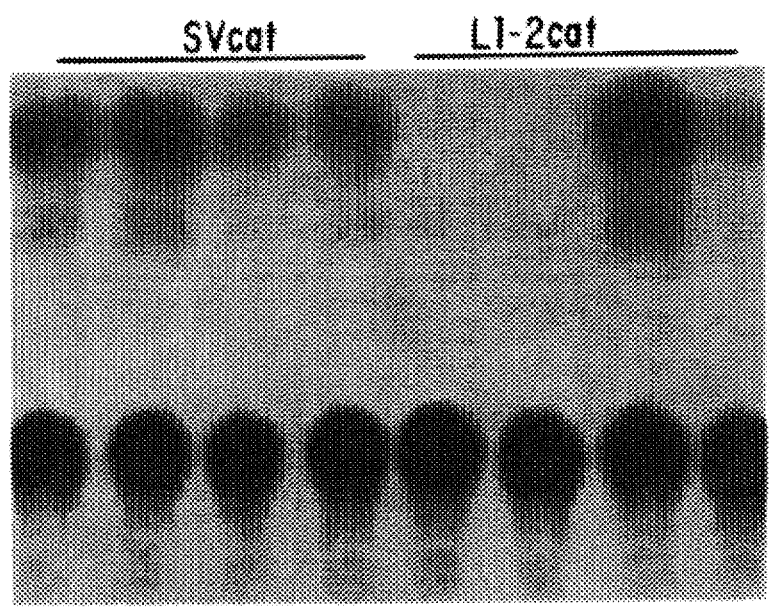

FIG. 6 Inhibition of LAP activity by IPTG. HeLa cells were plated out two days before transfection in normal media or media containing 10 mM IPTG. Transfections contained 2 μg of either pSV2CAT or pL1-2CAT alone or with 1 μg of pHCMVLAP348. Cells transfected in IPTG were fed with media containing 10 mM IPTG 16 hours after transfection. CAT assays were preformed as described in the text. The relative activities (RA) of each extract normalized to that produced by pSV2CAT are shown below the figure.

FIG. 7 Genetic selections for LAP producing cell lines.

(A) Vectors for selection of LAP producing cell lines. The SV40 early promoter is represented as an open box and the direction of transcription is indicated by an arrow. Operators are indicated as stippled boxes. The neo gene from pSV2neo is indicated as a hatched box and the SV40 T-antigen gene is indicated by the long grey box. The caret indicates the SV40 early intron, and the short grey box within the neo construct indicates the SV40 polyadenylation signal from pSV2neo.

(B) Indirect immunofluorescence of HeLa cell lines stably transfected with LAP348. HeLa cell lines LAP neo2b and LAPneo6b were fixed and stained for LAP348 as described in Experimental Procedures. No true fluorescent signal was observed with naive HeLa cells.

(C) Expression of inducible CAT vectors in LAP cell lines. HeLa cells, Wild-type SV40 T-antigen transformed rat embryo fibroblast (REF) cells (SVREF), or cell lines derived from cotransfections described above were transfected with either pSV2cat or pL7cat as indicated. Cells derived from cotransfection of HeLa or REF cells are indicated.

Figure 8:
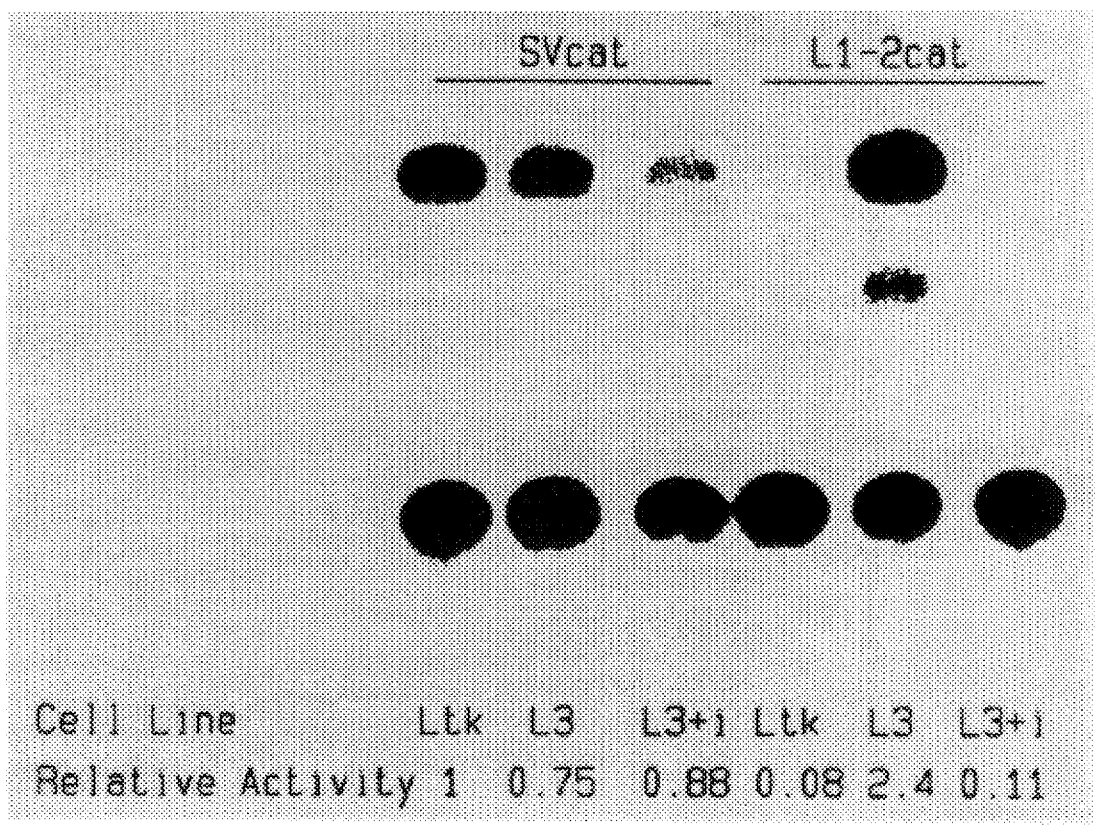

FIG. 8 Inhibition of LAP348 activity of L3 cells by IPTG. Either LTK or L3, or L3 cells grown in the presence of 10 mM IPTG (L3+i) for 48 hours before transfection, were transfected with either pSV2cat or pL1-2cat as indicated. The relative activity of the extracts normalized to that produced by SV2cat in Ltk- cells are shown below.

Figure 9:
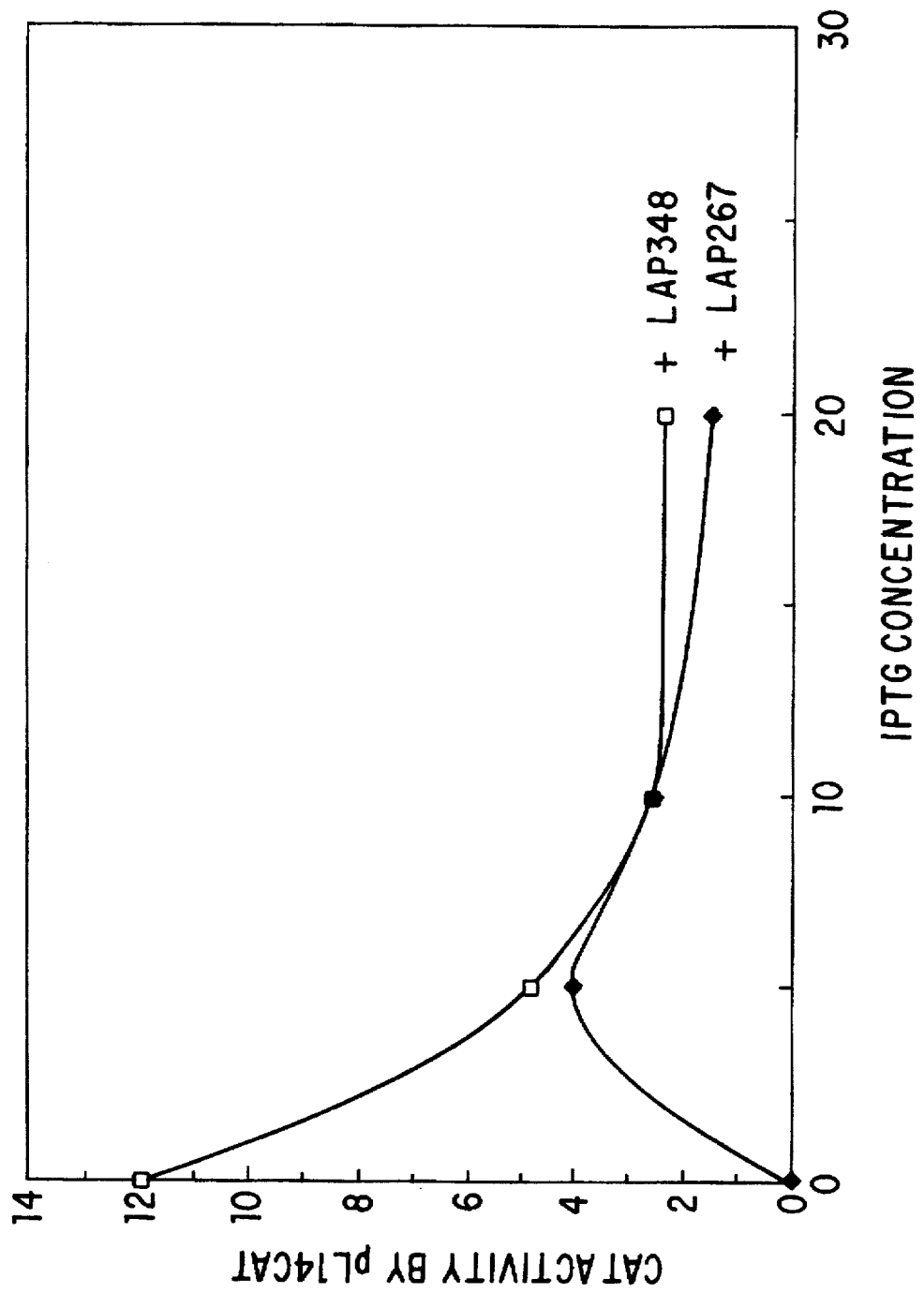

FIG. 9 Reverse-regulatory effect of IPTG on transactivator activity of LAP267 at 39.5° C.

5. DETAILED DESCRIPTION OF THE INVENTION

For purposes of clarity of disclosure, and not by way of limitation, the detailed description of the invention is divided into the following subsections:

(i) chimeric transactivator proteins of the invention (ii) construction of genes responsive to the chimeric transactivator proteins of the invention; and (iii) utility of the invention.

5.1. Chimeric Transactivator Proteins of the Invention

The chimeric transactivator proteins of the invention comprise (i) a functional portion of a DNA binding protein and (ii) a functional portion of a transcriptional activator protein.

The DNA binding protein may be derived from any vertebrate, nonvertebrate, fungal, plant, or bacterial source including but not limited to Gal 4 (Keegan et al., 1986, Science 231:699–704), ADR1 (Hartshorne et al., 1986, Nature 320:283–287), SwI (Stillman et al., 1988, EMBO J. 7:485–495) and as generally reviewed in Johnson et al. (1989, Annual Rev. Biochem., 58:799–839). It may be a repressor protein, such as, for example, the lexA repressor. In preferred embodiments of the invention, the DNA binding protein is the bacterial lac repressor. Building a chimeric transactivator protein on a backbone derived from a bacterial DNA binding protein may confer specificity on the transactivator protein, because it may target the transactivator sequences to binding sites engineered into the proximity of genes of interest. Herein, the term "gene" may be construed to refer to a DNA sequence encoding a mRNA as well as its cis-acting control elements. Because DNA sequences homologous to the bacterial DNA binding sites are unlikely to occur frequently in the mammalian genome, the chimeric transactivator proteins of the invention may be used to selectively control the expression of genes of interest engineered to comprise the appropriate bacterial DNA binding sequence. Utilization of the lac repressor offers the advantage that this protein has been extensively characterized, thus allowing for rational modification of the molecule to effect useful functions.

The present invention relates to transactivating proteins which are capable of functioning in vertebrate cells and may include naturally occurring transcriptional transactivating proteins or domains of proteins from eukaryotic cells including vertebrate cells, viral transactivating proteins or any synthetic amino acid sequence that is able to stimulate transcription from a vertebrate promoter. Examples of such transactivating proteins include, but are not limited to, the lymphoid specific transcription factor identified by Muller et al. (1988, Nature 336:544–551), the fos protein (Lucibello et al., 1988, Oncogene 3:43–52); v-jun protein (Bos et al., 1988, Cell 52:705–712); factor EF-C (Ostapchuk et al., 1989, Mol. Cell. Biol. 9:2787–2797); HIV-1 tat protein (Arya et al., 1985, Science 229:69–73), the papillomavirus E2 protein (Lambert et al., 1989, J. Virol. 63:3151–3154) and the adenovirus E1A protein (reviewed in Flint and Shenk, 1989, Ann. Rev. Genet.). In preferred embodiments of the invention, the transactivating protein is Herpes simplex virus VP16 (Sadowski et al., 1988, Nature 335:563–564; Triezenberg et al., 1988, Genes and Dev. 2:718–729).

According to the invention, DNA sequences encoding the DNA binding protein and the transactivating protein are combined so as to preserve the respective binding and transactivating properties of each. In various embodiments of the invention, the DNA encoding the transactivating protein, or a portion thereof capable of activating transcription, may be inserted into DNA encoding a bacterial DNA binding protein at a locus which does not completely disrupt the function of said DNA binding protein. Regions not required for function of DNA binding proteins or transcriptional transactivating proteins may be identified by any method known in the art, including analysis of mapped mutations as well as identification of regions lacking mapped mutations, which are presumably less sensitive to mutation than other, more functionally relevant portions of the molecule. The appropriate recombinant constructs may be produced using standard techniques in molecular biology, including those set forth in Maniatis (1982, Molecular Cloning: A Laboratory Manual (Cold Spring Harbor, N.Y., Cold Spring Harbor Laboratory)).

In preferred embodiments of the invention, the recombinant DNA constructs encoding the chimeric transactivator protein may further comprise a nuclear localization sequence, so that the chimeric transactivator protein is selectively concentrated in the cell nucleus. For example, nucleic acid sequence encoding the SV40 large T antigen nuclear localization signal, Pro-Lys-Lys-Lys-Arg-Lys-Val (Kalderon et al., 1984, Cell 39:499–509) may be placed in apposition to the transactivator protein encoding sequences.

Further, it may be necessary to change, using standard techniques, the initiator triplet of the bacterial DNA binding protein to ATG, in order to permit efficient translation of the chimeric transactivator protein within vertebrate cells.

The recombinant DNA construct encoding the chimeric transactivator protein may be placed under the control of a suitable promoter sequence. It may be desirable for the transactivator protein to be placed under the control of a constitutively active promoter sequence, although said transactivator protein may also be placed under the control of an inducible promoter, such as the metallothionine promoter (Brinster et al., 1982, Nature 296:39–42) or a tissue specific promoter. Promoter sequences which may be used according to the invention include, but are not limited to, the SV40 early promoter region (Bernoist and Chambon, 1981, Nature 290:304–310), the promoter contained in the long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the human cytomegalovirus (CMV) immediate early promoter/enhancer (Boshart et al., 1985, Cell 41:521–530), and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in erythroid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In one preferred specific embodiment of the invention, the chimeric transactivator protein is encoded by pHCMVLAP348, constructed according to methods set forth in Example Section 6, infra. Briefly, pHCMVLAP348 may be created by performing the following modifications of the lacI gene, using standard recombinant techniques: (i) the bacterial initiator GTG may be changed to ATG to form lacI$^{ATG}$; (ii) the 5' end of lacI$^{ATG}$ may be modified to include the SV40 large T antigen nuclear localization signal (supra) to create lacI 5'N1; (iii) a cassette encoding the carboxyl-terminal acidic domain between amino acids 369 and 488 of VP16 may be inserted in-frame into a PvuII site after codon for amino acid 348 of the lacI gene to create LAP348; and (iv) the resulting construct may be placed under control of the human cytomegalovirus (CMV) immediate early enhancer promoter (Boshart et al., 1985, Cell 41:521–530), a constitutive promoter.

In another preferred specific embodiment of the invention, the chimeric transactivator protein is encoded by pHCMVLAP267, which is identical to pHCMVLAP348 (supra) except that the VP16 segment is inserted after codon 267 of the lacI coding region. As will be discussed in greater detail in Section 5.3, infra, the activity of pHCMVLAP267 is temperature-sensitive and reverse-regulated by IPTG.

5.2. Construction of Genes Responsive to the Chimeric Transactivator Proteins of the Invention According to the invention, the chimeric transactivator proteins of the invention may be utilized to specifically regulate the expression of genes engineered to comprise transactivator responsive elements. These transactivator responsive elements should correspond to a nucleic acid sequence recognized and bound by the DNA binding protein used as the backbone of the chimeric transactivator protein. One or preferably more than one transactivator responsive element may be engineered to occur upstream, within, or downstream of the coding sequence of a gene of interest. It may be desirable to provide transactivator responsive elements in tandem. It may be less desirable in at least some cases to incorporate a transactivator responsive element downstream of the TATA box (for example, see FIG. 5).

In preferred embodiments of the present invention, lac is the bacterial DNA binding protein used as a backbone for the chimeric transactivator protein, and the transactivator responsive element is the lac operator sequence. As exemplified in Section 6 infra, chimeric transactivator proteins comprising lac sequences may activate transcription of a gene of interest (chloramphenical acetyl transferase (CAT), see Section 6) if one or more lac operators are in the proximity of the CAT gene, with 5' operator sequences functioning more effectively than 3' operator sequences. Tandem operators, spaced approximately 100 base pairs apart, appeared to be most effective. Interestingly, a lac operator located downstream of the TATA box appeared to repress transactivation.

The data shown in FIG. 5 demonstrated that LAP is bifunctional, that is, LAP can either repress or activate gene expression depending on the position of the operator (downstream of the promoter for repression and upstream of the promoter for activation). This ability allows LAP to be uniquely used as a bidirectional switch in that one gene can be turned on while another is turned off using the same treatment, including for example, treatment with IPTG or a temperature shift. This ability allows one to carry out a unique type of experiment that may be referred to as gene expression replacement. In such an experiment, the expression of a LAP-repressible gene may be replaced by expression of a LAP-inducible gene simply by adding IPTG or shifting temperature. A specific application for gene replacement would be to transform cells with any oncogene (or antioncogene) under the control of a promoter repressible by LAP and a mutant form of the oncogene under the control of a promoter inducible by LAP. Upon induction of LAP activity, the wild-type oncogene may be switched off while the mutant oncogene may be switched on, thus replacing the mutant for the wild-type oncogene product within the cell.

The ability to use LAP as a bidirectional switch also allows for negative auto-regulation of LAP protein synthesis. This is particularly important in that expression of strong transactivators is often toxic to cell. For example, if LAP was expressed from a promoter which itself was negatively regulated by LAP, once amounts of LAP sufficient to specifically regulate gene expression were produced within a cell, LAP would shut off its own synthesis. This would prevent LAP from being overproduced and thus reduce the toxicity of the transactivator. Such control of LAP synthesis might also be utilized to lower the basal expression from LAP inducible genes by repressing LAP synthesis in the off state with heterologous or homologous repressors.

5.3. Utility of the Invention

In general, the chimeric transactivator proteins of the invention may be used to selectively control the expression of genes of interest. For example, and not by way of limitation, the chimeric transactivator proteins of the invention may be placed under control of a constitutive promoter and may be used to constitutively increase the expression of a gene of interest associated with transactivator responsive elements, for example, when it is desirable to produce a particular gene product in quantity in a cell culture or in a transgenic animal. Alternatively, the transactivator protein may be placed under the control of a tissue-specific promoter so that the gene of interest is expressed in a particular tissue. In preferred embodiments of the invention, the chimeric transactivator function is inducible, so that the expression of a gene of interest, via transactivator responsive elements, may be selectively increased or decreased.

In order to more clearly present the usefulness of the invention, the utility of the invention will be discussed in the following subsections:

(i) properties of transactivating proteins;
(ii) selection procedures;
(iii) transgenic animals carrying the chimeric transactivating proteins of the invention; and
(iv) the creation of useful cell lines according to the invention.

5.3.1. Properties of Transactivating Proteins

The chimeric transactivating proteins possess the advantageous property of binding specifically to responsive elements homologous to DNA sequences recognized by the chimeric protein's DNA binding protein backbone. This property overcomes a disadvantage observed when transactivating proteins lacking DNA binding protein sequences are used to transactivate genes of interest; because transactivating proteins are often found to increase the transcription of a variety of genes in addition to the gene of interest, non-specific gene activation is observed. Furthermore, as was observed for lac bearing chimeric transactivating proteins, while transcription of most lac-operator bearing sequences was increased, expression of other sequences, such as the SV40 promoter, could be nonspecifically repressed (squelched) in the absence of a lac operator or were specifically repressed, dependent on the position of a lac operator sequence.

In preferred embodiments of the invention, the expression of the chimeric transactivator proteins is inducible by a chemical or physical agent. Inducibility provides the advantage of being able to significantly increase expression of a gene of interest for a controlled period of time. In preferred, non-limiting specific embodiments of the invention, the chimeric transactivator protein comprises a portion of the bacterial lac protein. The binding of the native lac protein to DNA is inhibited by isopropyl β-D-thiogalactoside (IPTG). As discussed in Section 6.2.5., infra, IPTG significantly reduced the transactivation resulting from pHCMVLAP348 expression, suggesting the IPTG may block the binding of transactivator protein to the lac operator. According to the invention, cells bearing DNA encoding a chimeric lac transactivator protein and a gene of interest engineered to comprise lac operator sequence may be cultured in the presence of IPTG such that transcription of the gene of interest is not activated; by removing IPTG from the culture medium, transactivation of the gene of interest may be induced.

It should be noted that all lac chimeric transactivator proteins may not have the same response to IPTG. For example, in another preferred embodiment of the invention, LAP267 transactivator protein (see Example Section 7, infra) is temperature sensitive, in that it has been observed to activate transcription at 32° C. but not at 39.5° C. Unexpectedly, IPTG has been found to "reverse-regulate" LAP267, in that it enables the protein to function at its non-permissive temperature. According to the invention, transcriptional activation of LAP267 may be achieved either by shifting LAP267-expressing cells from the non-permissive to the permissive temperature or by exposing cells cultured at the non-permissive temperature to IPTG.

5.3.2. Selection Procedures

According to the invention, it may be desirable to identify cells which express chimeric transactivator proteins. The presence of protein encoded by recombinant constructs may be detected using antibody specific for a component of the chimeric protein; for example, anti-lac antiserum was used to detect the presence of chimeric, lac-derived proteins (LAP proteins) in cells transfected with pHCMVLAP348 (see Section 6.2.1., infra). However, it would be preferable to detect the presence of transactivator function.

Transactivator function may be detected, according to the invention, using a marker gene encoding a selectable or otherwise identifiable product, comprising one or more transactivator responsive elements. Effective transactivator function should result in the detectable expression of the marker gene. Useful marker genes include, but are not limited to E. coli β-galactosidase (lacZ, LAC), chloramphenicol acetyl transferase (CAT), neomycin phosphotransferase (APH3'II, NPTII), nopaline synthetase (NOS), octopine synthase (OCS), firefly luciferase (luc) and bacterial luciferase (luxA and luxB) and transforming genes, including, but not limited to, known oncogenes including but not limited to those derived from DNA tumor viruses (e.g., T antigen genes from SV40 or polyoma viruses, E1A and E1B genes from adenoviruses, and other genes known to have tumorigenic potential derived from papillomaviruses and herpes viruses; reviewed in Bishop, 1985, Cell 42:23–38); retroviruses (e.g., v-abl, v-fes, v-fps, v.-fgr, v-src, v-erbA, v-erbB, v-fms, v-ros, v-yes, v-mos, v-ras, v-fos, v-myb, v-myc, v-ski, v-sis, v-rel, v-kit, v-jun, v-ets; reviewed in Bishop, 1985, Cell 42:23–38); cellular proto-oncogenes corresponding to the viral oncogenes, activated cellular oncogenes corresponding to viral oncogenes, or cellular oncogenes for which no viral counterpart has yet been described (e.g., c-neu, Hung et al., 1986, Proc. Natl. Acad. Sci. USA 83:261–264).

For example, and not by way of limitation, functional expression of the LAP348 transactivator protein in LAP348 transfected cells may be detected by further transfecting cells with a recombinant DNA construct comprising several lac operators and a gene (e.g., neomycin phosphotransferase, or neo) encoding a protein which confers antibiotic (e.g. G418) resistance. Cells which carry a functional LAP348 protein should actively express the neo gene and be G418 resistant (see Section 6.2.6., infra). It may be desirable to measure basal promoter activity, for example, by comparing the phenotype of cells comprising the marker gene construct with and without chimeric transactivator protein in order to ensure that marker gene is not expressed in the absence of chimeric transactivator protein, so as to confirm the sensitivity of the assay (refer to Section 6.2.6., infra ).

In various embodiments of the invention, it may be desirable to use a chimeric transactivator protein(s) to control the expression of a gene of interest which encodes a product that is not easily detectable. In these embodiments, it may be preferable to provide cells with (i) chimeric transactivator encoding DNA, (ii) a gene of interest comprising transactivator responsive elements, and (iii) a marker gene comprising transactivator responsive elements. The ability of the transactivator to control the expression of the gene of interest may be detected indirectly by assaying for the product of the marker gene.

5.3.3. Transgenic Animals Carrying the Chimeric Transactivating Proteins of the Invention The present invention provides for non-human transgenic animals carrying transgenes encoding chimeric transactivator proteins. These transgenic animals may further comprise a gene of interest under the control of transactivator-responsive elements. In various embodiments of the invention, the transactivator protein may constitutively enhance the expression of the gene of interest. Alternatively, the transactivator protein may only enhance the expression of the gene of interest under certain conditions; for example, and not by way of limitation, if the transactivator protein is LAP348, transactivator protein activity may be inhibited by administering IPTG, then induced to the transgenic animal ceasing administration of IPTG. In a further example, if the transactivator protein is LAP267, transactivator activity would normally be absent at 39.5° C., but could be induced by administering IPTG to the transgenic animal.

The recombinant DNA molecules of the invention may be introduced into the genome of non-human animals using any method for generating transgenic animals known in the art.

One method for the creation of transgenic mice for producing test animals is described below.

In general, the scheme presently employed to produce transgenic mice involves the following: male and female mice, from a defined inbred genetic background, are mated at midnight. Twelve hours later, the female is sacrificed and the fertilized eggs are removed from the uterine tubes. At this time, the pronuclei have not yet fused and it is possible to visualize them in the light microscope. Foreign DNA is then microinjected (100–1000 molecules per egg) into a pronucleus. Shortly thereafter fusion of the pronuclei (a female pronucleus or the male pronucleus) occurs and, in some cases, foreign DNA inserts into (usually) one chromosome of the fertilized egg or zygote. The zygote is then implanted into a pseudo-pregnant female mouse (previously mated with a vasectomized male) where the embryo develops for the full gestation period of 20–21 days. The surrogate mother delivers these mice and by four weeks the pups are weaned from the mother. To test these mice for the presence of foreign DNA, a portion of the tail (a dispensable organ) is removed and the DNA extracted. DNA—DNA hybridization (in a dot blot, slot blot or Southern blot test) is employed to determine whether the mice carry the foreign DNA. Of the eggs injected, on average 10% develop properly and produce mice. Of the mice born, an average one in four (25%) are transgenic for an overall efficiency of 2.5%. Once these mice are bred they pass along the foreign gene in a normal (Mendelian) fashion linked to a mouse chromosome. Mating two homozygous mice with the transgenic DNA means 100% of the offspring carry two copies of the transgene.

When this is done it is common that the mice carry tandemly repeated copies of the foreign gene (from 2–100 copies) at one chromosomal location or site.

The present invention is not limited to any one species of animal, but provides for any non-human animal species which may be appropriate. For example, mice, guinea pigs, rabbits and pigs, to name but a few, may provide useful transgenic systems.

Likewise, any method known in the art may be used to produce transgenic animals, including but not limited to, microinjection, transfection of DNA, and electroporation.

5.3.4. The Creation of Useful Cell Lines According to the Invention

In specific embodiments of the invention, chimeric transactivating proteins may be utilized to establish useful cell lines. For example, cell lines which exhibit differentiated cell function may be developed using inducible transactivating proteins according to the following method.

A non-human transgenic animal may be generated comprising transgenes encoding (i) an inducible chimeric transactivating protein and (ii) a transforming protein under the transcriptional control of transactivator responsive elements, such that the transactivating protein is not constitutively active in the transgenic animal and therefore, absent induction, the transforming protein is not expressed. Said animal may be sacrificed, or biopsies obtained, and various tissues of the animal may be prepared for cell culture and then cultured under conditions which induce transactivator function and consequently, expression of transforming protein. The cells may thus be maintained through successive generations, but may be allowed to resume differentiated cell function by the removal of the inducing agent.

In a preferred specific embodiment of the invention, a transgenic animal may be produced which carries a gene encoding LAP267 under control of a constitutive promoter (which may in all cells and tissues function or, alternatively, may function only in a single tissue type or cell type) also a gene encoding SV40 T antigen under control of a LAP responsive promoter. Because the body temperature of the mouse should inhibit the transactivator function of LAP267, SV40 T antigen should not be expressed in the live animal. This transgenic animal may be sacrificed, or biopsies may be obtained, and various tissues may be prepared for cell culture and then induced to express the SV40 T antigen transforming protein by either culturing the cells at 32° C. or, alternatively culturing the cells at 39.5° C. in the presence of IPTG. The resulting cell lines may be readily propagated, and may be allowed to resume differentiated functions by culturing the cells at a temperature high enough to inhibit LAP267 function in the absence of IPTG.

6. EXAMPLE: CONSTRUCTION OF ALLOSTERICALLY REGULATED LAP348 TRANSACTIVATING PROTEIN

6.1. Materials and Methods

6.1.1. Construction of LACI Derivatives

Plasmids were constructed using standard procedures (Maniatis et al., 1982, Molecular Cloning: A Laboratory Manual (Cold Spring Harbor, N.Y., Cold Spring Harbor Laboratory)). Synthetic oligonucleotides were prepared on an Applied Biosystems automated DNA synthesizer using phosphoamidite chemistry.

The lacI gene contained in the f1 hybrid phage f1 delta 47 (generously provided by J. E. LeClerc), a derivative of f1-K12 (Hayes et al., 1988, J. Mol. Biol. 201:239–246), was altered by in vitro mutagenesis according to the procedure described by Zoller and Smith (Zoller et al., 1984, DNA 3:479–488). f1 delta 47 differs from f1-K12 by a 47 bp deletion that removes the operator and creates an EcoRI site at the junction. The oligonucleotide 5'-CTGGTTTCATGTTAACCACCC-3' was used as a mutagenic primer to generate f1-lacI$^{ATG}$ by changing the initiator GTG to ATG and by creating an HpaI site immediately 5' to the lacI coding region.

Two complementary oligonucleotides, 5'-GATATCATGCCAAAAAAGAGAAAGGTA-3' and 5'-TACCTTTCTCTTCTTTTTTGGCATGATATC-3', which contains an EcoRV site and encodes an initiator Met (ATG is underlined) and the SV40 large T antigen nuclear localization signal Pro-Lys-Lys-Lys-Arg-Lys-Val (Kalderon et al., 1984, Cell 39:499–509), were phosphorylated, annealed and inserted at the new HpaI site of lacI$^{ATG}$ to generate lacI5'N1.

DNA containing lacI$^{ATG}$ was partially digested with HpaI, a BamHI linker was added, excised by digestion with EcoRI and the 1.2 kb BamHI-EcoRI fragment was then subcloned into pBR322. The EcoRI site was converted to a SalI site, and the BamHI-SalI lacI$^{ATG}$ fragment was inserted into pExpl, an expression vector containing the SV40 early promoter, the SV40 small t antigen splice site and the Ad5 E1B poly A addition site, to generate pExp1-lacI$^{ATG}$.

pHCMVlacI$^{ATG}$ was constructed by ligation of the EcoRI-HindIII fragment from pBC123 (generously provided by L. S. Chang), containing the human CMV promoter/enhancer between nucleotides-600 and +72 relative to the transcription start site (Boshart et al., Cell 41:521–530) the HindIII-PvuII fragment from pBR322 and the EcoRI-NruI fragment from pExp1-lacI$^{ATG}$ containing the lacI$^{ATG}$ gene, the small t antigen splice site and the E1B polyadenylation site. The SmaI-ApaI fragment from pHCMVlacI$^{ATG}$ was replaced with the EcoRV-ApaI fragment from lacI5'N1 to create pHCMVlacI5'N1. A 360 bp RsaI fragment encoding the last 120 amino acids of VP16 was isolated from pVP16-0, and cloned into the EcoRV site of pBSII (Stratagene Inc.). The VP16 coding region was then removed by partial digestion with SmaI and complete digestion with HindIII. The small 400 bp fragment was isolated and the HindIII overhang was filled using the Klenow fragment of E. coli DNA polymerase I and then ligated with pHCMVlacI5'N1 which had been partially digested with PvuII, creating pHCMVLAP317 and pHCMVLAP348. The LAP348 coding region was removed from pHCMVLAP348 by partial digestion with SstI and complete with BglII. The LAP348 gene was subcloned into pBSII and subsequently inserted into the human β-actin vector pBAP2 (Gunning et al., 1987, Proc. Natl. Acad. Sci. 84:4831–4835).

6.1.2. Construction of Reporter Constructs pSVE-CAT was created by insertion of the SphI-BamHI fragment of pSV2CAT into SphI-BamHI digested pFB69 (Barany, 1985, Gene 37:111–123), a derivative of pBR322. pL1CAT was created by insertion of the SphI-BamHI fragment of pSV2CAT into SmaI-BamHI digested pBSI (Bluescript vector KS+; Stratagene) such that the SV40 promoter was 150 bases downstream from the lac operator located in the vector. A synthetic lac operator DNA duplex with SalI cohesive ends was obtained by annealing the following two phosphorylated oligonucleotides: 5'-TCGACGGAATTGTGAGCGGATAACAATTG-3' 5'-TCGACAATTGTTATCCGCTCACAATTCCG-3'. pL1-1CAT and pL1-2CAT were created by insertion of one or two 29 bp synthetic operators, respectively, into the SalI site of pL1CAT. pL1-3CAT was created by inserting an additional operator into the XhoI site of pL1-2CAT. pL2CAT was created by insertion of the XhoI-BamHI fragment of pL1-2CAT into XhoI-BamHI digested pFB69. pL7CAT was created by ligation of a PvuII-EcoRV fragment containing the 4 lac operators of pL1-3CAT into the EcoRV site of pL1-2CAT. pL14CAT and pL21CAT were created by insertion of one or two copies of the operator-containing PvuII-EcoRV fragment of pL7CAT into the EcoRV site of pL7CAT. p3'L3CAT and p3'L7CAT were created by insertion of either the ApaI-ClaI (pL1-3CAT) or the PvuII-EcoRV (pL1CAT) into the EcoRV site of site of pSVE-CAT. pICP0L1CAT was created by insertion of the small EcoRI fragment of pIGA65 (Gelman and Silverstein, 1987, J. Viol. 61:2286–2296) into EcoRI digested pCAT, which contains the CAT gene and SV40 splice and polyadenylation signals from pSV2CAT inserted into the EcoRV site of pBSI. pICP0 was created by insertion of the pICPOCAT gene without the vector-contained operator sequence in the EcoRV site of pFB69.

Plasmids pX-8, pX-58, pX-100, pS-312, and pS-232, described in Fromm and Berg (1982, J. Mol. Appl. Genet. 1:457–481) were generously provided by P. Berg. The synthetic lac operator (described supra) was cloned in the XhoI site of pX-8 (deletion endpoints 3 and 5237 in the SV40 DNA sequence (to generate pSV$^{Lp1}$. Deletion mutants pX-58 (deletion endpoints 53 and 5237) and pS-312 (deletion endpoints 346 and 34) or X-100 (deletion endpoints 108 and 5237) and pS-232 (deletion endpoints 346 and 114) were recombined by ligation in the presence synthetic lac operator and single insertions of lac operator were identified to construct pSV$^{Lp2}$ and pSV$^{Lp3}$, respectively. A plasmid, designated pSV$^{L2p3}$, containing two tandem operators at position 3 was also isolated. The KpnI-NcoI fragment from pSV$^{Lp3}$ was substituted for the corresponding fragment in pSV$^{Lp1}$ to generate pSV$^{Lp1-3}$. Insertion of operators was first detected by the appearance of blue colonies on plates containing X-gal (Boehringer Manheim) after transformation of HB101 cells, due to titration of the endogenous lac repressor with a high copy plasmid bearing the operators. Various CAT reporters were constructed by excising the Sau3AI-HindIII fragment encompassing the SV40 early promoter from pX-8, pSV$^{Lp1}$, pSV$^{Lp2}$, pSV$^{Lp3}$ and pSV$^{Lp1-3}$, and then inserting each fragment into BglII-HindIII digested pA10CAT$_2$ (Laimins et al., 1982, Proc. Natl. Acad. Sci. USA 79:6453-6457).

pL1-3neo was created by insertion of the SfiI-BamHI fragment of pSV2neo into sfiI-BamHI digested pL1-3CAT. pL2T-antigen was created by insertion of the SphI-BamHI fragment of pSV$^{L2p3}$T-antigen into SphI-BamHI digested pFB69.

6.1.3. Cell Culture and Transfections

Monolayer HeLa and Ltk-cell lines were maintained in Dulbecco's modified Eagles medium (DME) supplemented with 10% calf serum. Primary REF cells (generously provided by C. Finlay) and transformants were maintained in DME medium supplemented with 10% fetal calf serum.

Cells were transfected by the calcium phosphate precipitation method as previously described (Wigler et al., 1979, Proc. Natl. Acad. Sci. USA 76:1373-1376). For transient expression assays, 50-70% confluent 100 mM plates of cells were incubated overnight after addition to the media of a 1 ml precipitate containing 2 µg of reporter and 1 µg of effector plasmids and carrier DNA (high molecular weight calf thymus DNA) for a total of 25 µg of DNA. The media and precipitate were removed and replaced with fresh media the next morning.

For stable transformation assays, G418$^r$ HeLa and Ltk-cells were selected with either 0.5 or 1 mg per ml G418, respectively. Individual G418$^r$ colonies and transformed REF foci were isolated with cloning cylinders and progated in appropriate media.

6.1.4. Cell Labeling and Immunoprecipation Analysis

Antibodies were raised in rabbits against purified lac repressor (generously provided by J. Borowiec and J. Gralla) by standard procedures.

For immunoprecipitation analysis, HeLa cells (10$^6$ cells/10 cm dish) were transfected using 10 µg of each lac derivative and 2 µg pAd5VAI/II, a plasmid encoding adenovirus type 5 (Ad5) VA RNA genes which has been shown to enhance expression of cotransfected genes (Kaufman, 1985, Proc. Natl. Acad. Sci., USA 82:689-693). The DNA precipitates were left on the cells for 4 hours, followed by incubation for 3 minutes with 15% glycerol in PBS. Cells were labeled with $^{35}$S-methionine 46-48 hours after transfection.

For metabolic labeling with $^{35}$S, HeLa cells were washed with methionine-free DMEM and then incubated for 2 hours in methionine-free medium containing 2% calf serum and 100 µCi/ml $^{35}$S translabel (ICN). Labeled cell lysates were prepared and immunoprecipitations were performed as described (Sarnow et al., 1984, J. Viol. 49:692-700), except for the use of RIPA buffer (50 mM Tris pH 7.5, 150 mM NaCl, 0.1% SDS, 0.1% Triton X-100, 0.1% DOC). Aliquots of precleared lysates (10$^7$ CPM) were incubated with 2 µl rabbit preimmune or immune serum for 1 hour on ice. Fixed, prewashed Staphylococcus aureus cells (Pansorbin; Calbiochem) were added (25 µl of 10% w/v suspension) and incubation continued for 10 minutes on ice. Cells were pelleted, washed three times in RIPA buffer and once in TEN (10 mM Tris pH 7.4, 1 mM EDTA, 50 mM NaCl). Samples were resuspended in 15 µl loading buffer (2.5 mM Tris pH 6.8, 2.5% SDS, 100 mM dithiothreitol, 10% glycerol, 0.005% pyronin Y), boiled for 5 minutes and loaded onto a 10% SDS-polyacrylamide gel. After electrophoresis, gels were fluorographed with Resolution (E. M Corp), dried and exposed to Kodak XAR film at −70° C.

6.1.5. Indirect Immunofluorescence

Subconfluent cells (LAPneo2b and LAPneo6b) and transfected HeLa cells grown in 35 mm dishes were washed three times with PBS, fixed with PBS containing 4% formaldehyde for 10 minutes, and permeabilized with 0.1% Triton X-100 in PBS for 2 minutes. Cells were washed five times with PBS and then incubated for 1 hour with rabbit immune serum against lac repressor diluted 1:100 with 5% goat serum in PBS. Cells were washed five times with PBS containing 0.5% BSA and 0.1% Tween 20, and then incubated for 1 hour with fluorescein-conjugated goat anti-rabbit antibody (Jackson ImmunoResearch Laboratories, Inc.) diluted to 25 µg/ml with 0.5% BSA and 0.1% Tween 20 in PBS. Cells were washed five times with PBS containing 0.1% Tween 20, once with PBS and analyzed by fluorescence microscopy.

6.1.6. RNA Analysis

Cytoplasmic RNA was isolated and digested with DNase 1 (Promega Inc.) RNase protection assays were carried out as described in Melton et al. (1984, Nucl. Acids Res. 12:7035-7056) using 20 µg of cytoplasmic RNA and hybridized with approximately 1×10$^5$ CPM of RNA probe prepared with [$^{32}$P]-UTP (less than 2000Ci/mmol; NEN). RNase digested samples were fractionated on a denaturing 5% polyacrylamide sequencing gel, dried and exposed to XAR-5 film for autoradiography.

6.1.7. CAT Assays

Cells were harvested 44-48 hours after transfection and CAT assays performed essentially as described (Gorman et al., 1982, Mol. Cell Biol. 2:1044-1051). Equal amounts (30-200 µg) of protein were used in each experiment. CAT activity was quantitated by thin layer chromatography and liquid scintillation counting of spots. Extracts that converted greater than 80% of the chloramphenicol in an assay were diluted appropriately to ensure linearity of the assay.

6.2. Results

6.2.1. Construction of LACI/VP16 Fusion Proteins

The structure of the lacI genes used for this study are shown schematically in FIG. 1A. In order to facilitate expression in mammalian cells the bacterial initiator GTG was changed to ATG, creating lacI$^{ATG}$. The 5' end of lacI was further modified to include the nuclear localization signal from the SV40 large T-antigen (Kalderon et al., 1984, Cell 39:499-509) generating lacI5'N1. When expressed in mammalian cells, both lacI$^{ATG}$ and lacI5'N1 functioned to efficiently repress transcription from promoters containing appropriately positioned lac operator sequences. The results with lacI5'N1 demonstrate that extending the amino terminus of lac repressor with the nuclear localization signal does not significantly interfere with operator binding.

Figure 1B:
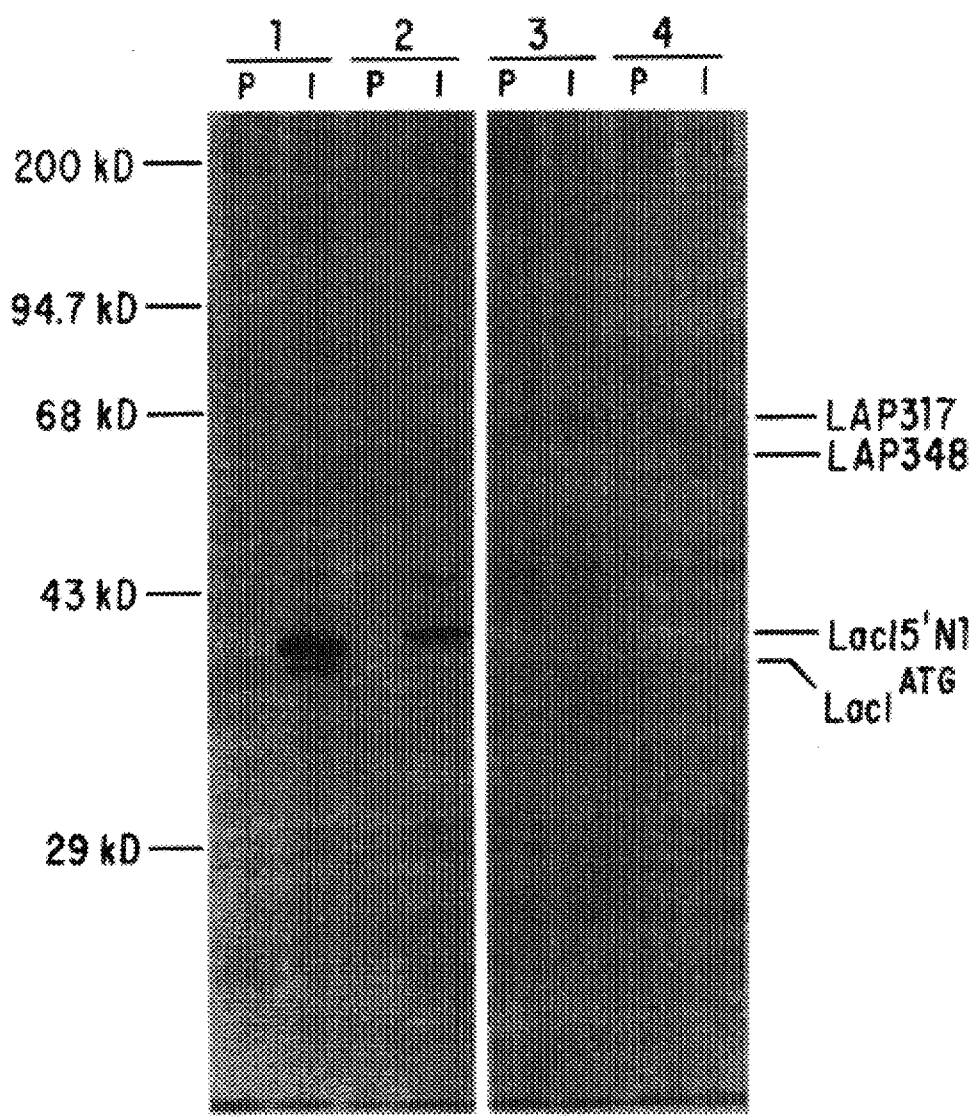

Two LAP constructs were generated by modification of lacI5'N1. A cassette encoding the carboxyl-terminal acidic domain between amino acids 369 and 488 of VP16 was inserted in-frame into either of two PvuII sites, after the codons for amino acids 317 or 348 of the lacI gene, creating LAP317 and LAP348, respectively. This strategy was chosen for two reasons. First, the two PvuII sites were within a region of the lacI gene with very few mapped mutations, suggesting that this region might be dispensible or independent from the domains involved in DNA binding, dimerization, and inducer binding (see Beyreuther 1978, In The Operon. J. H. Miller and W. S. Reznikoff III, eds. (Cold Spring Harbor, N.Y., Cold Spring Harbor Laboratory) and Miller 1978, In The Operon. J. H. Miller and W. S. Reznikoff III, eds. (Cold Spring Harbor, N.Y., Cold Spring Harbor Laboratory) for review). Furthermore, previous experiments demonstrated that insertion of a nuclear localization signal at amino acid 348 did not appear to alter the activity of the repressor. Second, genetic analysis of the lacI gene suggested that the carboxy-terminal 40 amino acids including the last eight amino acids of the repressor might be required for tetramerization. Thus, the fusion proteins were constructed such that every amino acid of lacI was conserved and the carboxy-terminus was left intact. Each coding region was placed under control of the human cytomegalovirus (CMV) immediate early enhancer promoter (Boshart et al. 1985, Cell 41:521–530) and these constructs were used in all transient assays presented in this study.

lacI-related proteins were detected by immunoprecipitation with anti-lacI rabbit polyclonal antiserum 48 hours after transfection of HeLa cells (FIG. 1B). A predominant 41 kd protein was detected following transfection with lacI$^{ATG}$; whereas, the protein detected after transfection with lacI5'N1 was slightly larger due to the nuclear localization signal. Both LAP317 and LAP348 migrated more slowly than expected with apparent molecular weights of 68 and 61 kd, respectively. This observation is not surprising in that many proline-rich nuclear proteins, such as p53 and VP16, have much slower mobilities on SDS-polyacrylamide gels than predicted by amino acid sequence (Zakut-Houri et al. 1983, Nature 306:594–597; Pellet et al. 1985, Proc. Natl. Acad. Sci. USA 82, 5870–5874). The reason for the different mobilities of LAP317 and LAP348 is not known but must be related to the location of the VP16 insertion within the lacI coding region. Consistently less LAP compared to lac repressor protein was detected, even though equal amounts of DNA were transfected and equal amounts of $^{35}$S-labeled extracts were used for immunoprecipitations. This might be due either to changes in protein stability or to effects of the LAPs on the CMV promoter.

The intracellular location of lacI derivatives was determined by indirect immunofluorescence. The fluorescent micrographs of cells transfected with either lacI$^{ATG}$, lacI5'N1 or LAP348 are compared in FIG. 1C. lacI$^{ATG}$ was present in approximately equal amounts in both the nuclear and cytoplasmic compartments. In contrast, the majority of the fluorescent signal observed after transfection with either lacI5'N1 or LAP348 was in the nucleus. Immunoprecipitation of fractionated cell extracts from transfected HeLa cells confirmed that almost all of the lacI5'N1 was present in the nuclear compartment, whereas lacI$^{ATG}$ was distributed equally in both cytoplasm and nucleus.

Figure 2A:
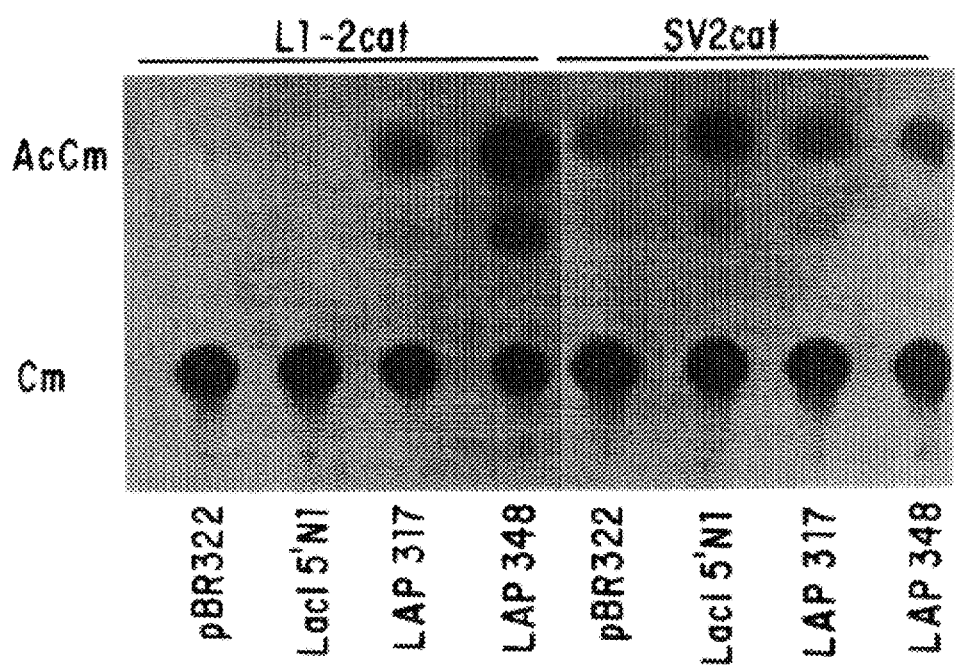

6.2.2. LAP317 AND LAP348 Activate Expression from an SV40 Promoter Containing lacI Sequences The ability of LAPs to activate suitable promoters was tested by cotransfection assays in HeLa cells. The first reporter tested, pL1-2CAT, consisted of a chloramphenicol acetyltransferase gene (CAT) under control of the SV40 promoter, lacking its enhancers, but linked to 3 lac operators. As a control for specificity, similar cotransfections were carried out with pSV2CAT (Gorman et al. 1982, Mol. Cell Biol. 2:1044–1051), which contains the endogenous SV40 enhancer but no lac operator sequences. Cellular extracts were prepared 48 hours after transfection and assayed for CAT activity (FIG. 2A). Expression from pSV2CAT was not significantly affected by cotransfection with either LAP construct. Very low levels of activity were detected after cotransfection of pL1-2CAT with either pBR322 or pHCMVlacI5'N1; however, high levels of CAT activity were observed after cotransfection of pL1-2CAT with either pHCMVLAP317 or pHCMVLAP348. Cotransfection with pHCMVLAP348 resulted in the production of significantly higher amounts of CAT activity as compared with pHCMVLAP317.

Figure 2B:
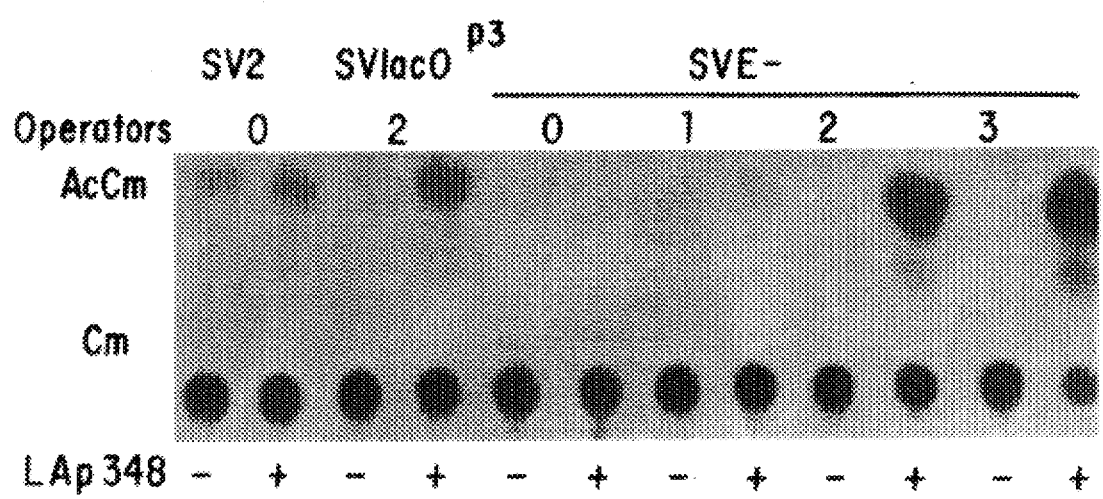

The effects of LAP348 on expression from the SV40 promoter with or without the enhancer were further examined by contransfection assays in HeLa cells as shown in FIG. 2B. Although LAP348 had no significant effect on pSV2CAT expression (lanes 1 and 2), LAP348 activated expression from pSVLP3CAT (lanes 3 and 4) which contains the SV40 enhancer and a single operator sequence between the enhancer and the Sp1 binding sites. Thus, operator-dependent activation occurred irrespective of the SV40 enhancer. The effects of LAP348 on expression of enhancerless SV40 CAT genes containing a single or multiple operators were also examined. LAP348 had no effect on expression of enhancerless SV40 construct, pSVE-CAT (lanes 5 and 6). The presence of a single operator located approximately 150 bp upstream of the SV40 promoter in pL1CAT allowed for activation (lanes 7 and 8). The insertion of 1 or 2 additional operators 40 bp upstream of the Sp1 binding sites of the SV40 promoter present in pL1-CAT and pL1-2CAT, respectively, greatly enhanced activation by LAP348 (compare lanes 8, 10 and 12). Thus, activation was dependent on the number of operators and multiple operators acted synergistically.

The structures of the promoters used to drive CAT expression are diagrammed in FIG. 3 along with their relative activities after cotransfection with pBR322 DNA or with LAP348. The relative activities represent the averages derived from 3–5 independent transfection experiments. The basal SV40 promoter used for these experiments contains the 21 base pair (bp) repeats of the SV40 promoter, which includes multiple binding sites for the transcriptions factor Sp1, the TATA box, origin of replication and normal transcription start sites. The basal activity of expression of the enhancerless SV40 promoter (pSVE-CAT and derivatives ) was normally undetectable in these assays (less than 0.02 of the activity produced by the SV40 enhancer promoter).

pL1CAT, which contains a single operator about 150 bp of the SV40 promoter produced about a tenth of the CAT activity of pSV2CAT upon activation by LAP348. pL2CAT which contains two tandem operators about 40 bp upstream of the SV40 promoter produced 2–3 fold higher levels of CAT than pL1CAT. In contrast, reporters containing the 150 bp upstream operator and either 1, 2 or 3 tandem operators (pL1-1CAT, pL1-2CAT or pL1-3CAT, respectively) inserted 40 bp upstream of the SV40 promoter produced significantly higher levels of CAT, 1.6 to 3 times that produced by pSV2CAT. Thus, there was a synergistic effect of multiple operators on activation when the operators where separated by a small distance. The reason for the spacing requirement is unclear, especially in light of the observations made by others that tandem operators increase the ability of lac repressor to inhibit expression from appropriate promoters in mammalian cells (Hu and Davidson, 1987, Cell 48:555–556). One explanation for this observation is that the increased size of LAP compared with lac repressor protein or the recruitment of additional cellular proteins by the VP16 sequences might prevent binding of two LAP tetramers to adjacent operators. Alternatively, the spacing of operators might only be important for efficient activation.

These data suggested that a functional unit for highly efficient activation consists of a set of spaced operators. Based upon this information, reporter plasmids containing tandem arrays of the spaced operators used in pL1-2CAT and pL1-3CAT were constructed and analyzed (FIG. 3). Although little difference in CAT expression was observed when pL1-2CAT and pL1-3CAT were compared, constructs containing tandem arrays of the spaced sets of operators showed enhanced levels of activation by LAP348. pL7CAT consisting of the tandem A and B operator repeats produced approximately 10 times as much CAT activity as pSV2CAT. A reporter containing 14 operators (pL14CAT) consisting of a tandem duplication of the L7 operators with the structure ABAB), produced two- to three-fold greater amounts of CAT activity than pL7CAT resulting in production of approximately 20 times as much CAT as pSV2CAT. Finally, pL21CAT, containing three tandem copies of the pL7CAT operators produced on average higher levels of CAT, approximately 30 times that by pSV2CAT. Because expression of pL14CAT and pL21CAT were not readily detectable in the absence of LAP, we infer from these experiments that expression was induced at least 1000- to 1500-fold by LAP348 under these transfection conditions (20.3 or 31.0 divided by 0.02, the lowest detectable level of expression; FIG. 3).

LAP348 was also activated expression of the SV40 promoter when operator sequences from pL7CAT were placed 3' to the CAT gene of pSVE-CAT (p3'L7CAT), although the amount of CAT produced was significantly lower than observed with the reporter containing the same operators just upstream of the promoter (pL7CAT). Thus, the operators act as a LAP-inducible enhancer. A reporter construct (p3'L3) containing a tandem array of 3 operator sequences 3' to the CAT gene produced low amounts of CAT upon activation by LAP348. This observation supports the conclusion stated above that activation through spatially separated operators is significantly more efficient than that achieved through tandem operators.

In order to confirm that LAP348 did not retain any specificity for VP16 responsive elements (the TAATGARAT elements), induction assays were also carried out with CAT genes under the control of the HSV ICP0 promoter. Expression from the ICP0 promoter of ICP0CAT, which contains multiple TAATGARAT elements, was not affected by LAP348 (FIG. 3). Thus the transplanted activation domain of VP16 did not retain any of its original sequence specificity. An ICP0 promoter construct containing a single operator placed downstream of the CAT gene (pICP0L1CAT) was activated by LAP348, demonstrating that activation by LAP is not restricted to the SV40 promoter.

It should be noted that LAP348 consistently inhibited expression, apparently nonspecifically, of pSV2CAT. Even under the conditions used in the above transfections (2 μg of CAT vector and 1 μg of LAP348) LAP348 inhibited expression from pSV2CAT approximately two-fold. Increasing the amount of LAP greatly inhibited pSV2CAT expression compared to lacI5'N1. One possible explanation for this observation is that overproduction of the strong activator domain of VP16 may sequester cellular transcription factors, poisoning the transcription machinery. This phenomenon, previously referred to as squelching, may account for the observation that less LAP was produced in transient assays than lacI5'N1 (FIG. 1B), perhaps reflecting an autoinhibitory effect on transcription from the CMV promoter.

6.2.3. LAP348 Acts by Increasing the Level of mRNA

Figure 4A:
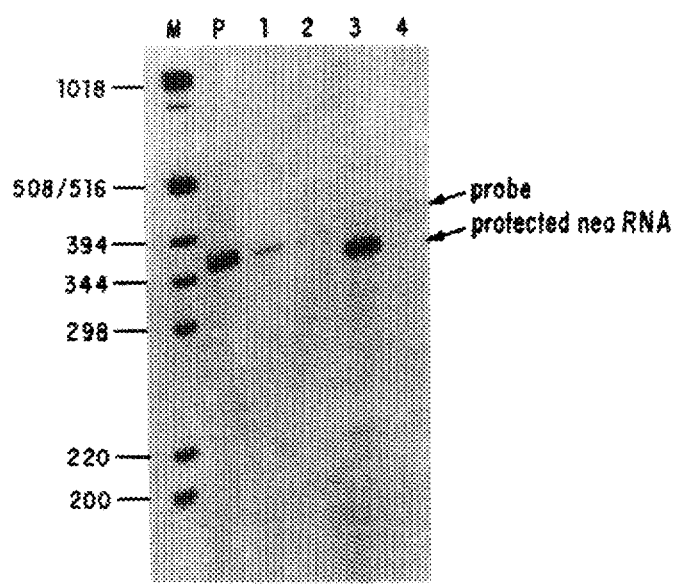
Figure 4B:
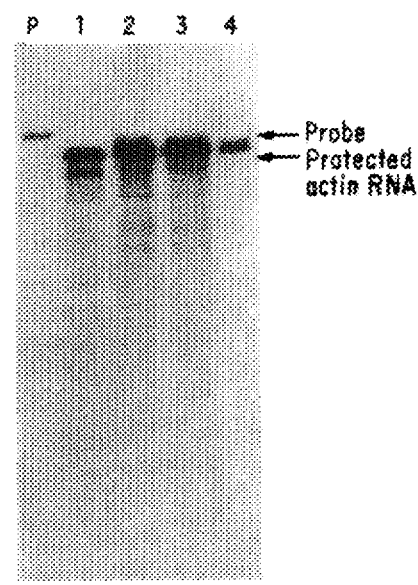

The specificity for activation by LAP348 and the characterized transcriptional activation function of the VP16 domain are consistent with LAP acting at the level of transcription. In order to confirm this level of cytoplasmic RNA produced by pL1-3neo, a neomycin phosphoribosyl transferase gene placed under control of the pL1-3CAT promoter (diagrammed in FIG. 7A), was measured after transfection alone or with LAP348 using an RNase protection assay (Melton et al., 1984, Nucl. Acids Res. 12:7035–7056) as shown in FIG. 4A.

The neo gene was used in this experiment because detection of the neo mRNA was more reproducible as compared with that of the CAT mRNA (data not shown). This observation was likely due to the reported instability of the CAT message (Laimonis et al., 1986, Proc. Natl. Acad. Sci. USA 83:3151–3155). The neo probe used was derived from pT7neo-320 (Jones and Cole, 1987, Mol. Cell. Biol. 7:4513–4521) and is approximately 360 nucleotides long, consisting of neo sequences from the HindIII-BglII sites of pSV2neo flanked by vector sequences, and protects an RNA fragment of approximately 320 nucleotides. Although extremely low amounts, if any, of the protected neo RNA were detected after transfection of pL1-3neo alone (lane 2), the protected neo RNA were readily detected when pL1-3neo was cotransfected with LAP348 (lane 3) supporting the notion that LAP acts at the transcriptional level. The protected neo RNA was not detected after transfection with either carrier DNA or with the LAP348 vector alone (lanes 1 and 4). Parallel protection assays carried out with a human β-actin probe (FIG. 4B) indicated that all RNAs were intact and that similar amounts of RNA were used.

6.2.4. LAP348 can Act as a Repressor or an Activator in a Position Dependent Fashion The lac repressor has been shown to block transcription of mammalian promoters containing suitably placed operator sequences. Thus, it was of interest to determine if LAP348 could also specifically repress gene expression. The effects of LAP348 on expression of a set of SV40 promoter/enhancer CAT constructs containing single lac operators at various positions after transfection into HeLa cells were determined. As shown in FIG. 5 the promoters contained operators either at the SV40 origin of replication immediately downstream of the TATA box (position(p)1; pSV$^{Lp1}$CAT), between the 21 bp repeats and the TATA box (p2; pSV$^{Lp2}$CAT), between the 72 bp repeats and the 21 bp repeats (p3; pSV$^{Lp3}$CAT), or at both p1 and p3 (pSV$^{Lp1-3}$CAT). Transfections were carried out with 2 μg of CAT vector and 5 μg of plasmids expressing the lac derivatives, concentrations of plasmids which were determined to be optimal for repression. Also, pX-8CAT (Fromm and Berg, 1982, J. Mol. Appl. Genet. 1:457–481), a construct containing an SV40 promoter with a XhoI linker at p1 was used as a control (pSV$^{Lp1}$CAT was derived from pX-8). Both lacI5'N1 and LAP348 inhibited expression from pSV$^{Lp1}$CAT (FIG. 5). LAP348 inhibited expression from pSV$^{Lp1}$CAT to an approximately five-fold greater extent than that observed for pX-8. Although lacI5'N1 had less of an inhibitory effect on constructs with operators at p2 and p3, LAP348 enhanced expression from these constructs two and five-fold, respectively. While an operator at p3 allowed for transactivation by LAP, a construct containing operators at both p1 and p3 was repressed by LAP. Thus, the ability of LAP to activate or repress the SV40 promoter was dependent on the position of the operator.

6.2.5. LAP is Allosterically Regulated by IPTG

IPTG regulates the lac repressor by greatly lowering the binding affinity for its specific operator sequence (Riggs et al. 1970, J. Mol. Biol. 48:67–83). The ability of IPTG to regulate LAP activity was examined by cotransfection assays with or without 10 mM IPTG in the growth medium. As shown in FIG. 6, LAP348 greatly activated expression from pL1-2CAT (lanes 5 and 7) but not from pSV2CAT (lanes 1 and 3). Although IPTG had no effect on expression of pSV2CAT either in the presence (lanes 2 and 4) or absence of LAP348 (lanes 1 and 3), IPTG reduced the level of activation of pL1-2CAT by greater than 10 fold (lanes 7 and 8). Thus, LAP348 retained functions needed for allosteric regulation. A low level of activation of pL1-2CAT was still observed, however, even in the presence of IPTG. These data may indicate that LAP348 is not as responsive to IPTG as the wild-type repressor or that intracellular concentration of IPTG was not great enough to inactivate LAP348. In this regard, other workers have noted that the response of the wild-type lac repressor to IPTG in mammalian cells is also slow and incomplete (Hu and Davidson 1987, Cell 48:555–566; Figge et al. 1988, Cell 52:713–722).

6.2.6. Genetic Selections for Production of LAP Producing Cell Lines

In order to facilitate the installation and maintenance of the LAP system into a desired cell type, positive selection schemes for LAP expression were developed. The two selectable vectors are diagrammed in FIG. 7A. The first, pL1-3neo, contains the operators and SV40 early promoter from pL1-3CAT linked to the neo gene from pSV2neo (Southern and Berg 1982, J. Mol. Appl. Genet. 1:327–341) and can be used to select for G418 resistant (G418$^r$) clones from established cell lines. The second vector, pL2T-antigen, consists of the SV40 large and small tumor antigen genes linked to an enhancerless early promoter and two tandem operators. This vector was used for selection of transformed foci in primary rat embryo fibroblasts (REF cells). These vectors were transfected alone or cotransfected with pHβA348 (LAP348 under the control of the human β-actin promoter) into the appropriate cell line as indicated in Table I.

TABLE I

Number of Colonies and Foci[a]

| Cell | Marker | — | LAP348 | LAP + clones[b] |
|---|---|---|---|---|
| HeLa | pL1-3neo | 6 | 47 | 6/6 |
| Ltk | pL1-3neo | >200 | 75 | 1/7 |
| REF | pL2 T-antigen | 0,0 | 31,34 | 6/6 |

Figures 7A, 7B:
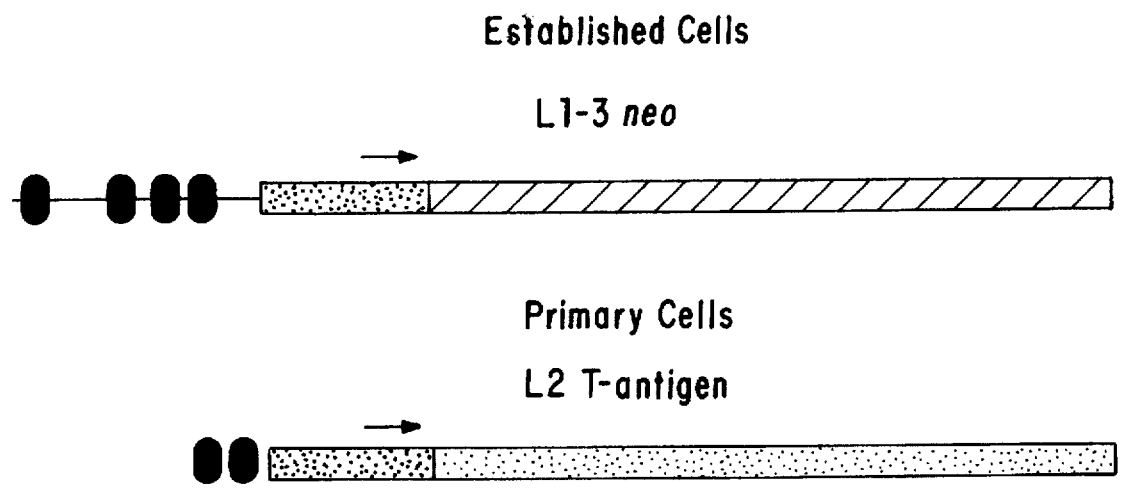
Figures 7C, 7D:
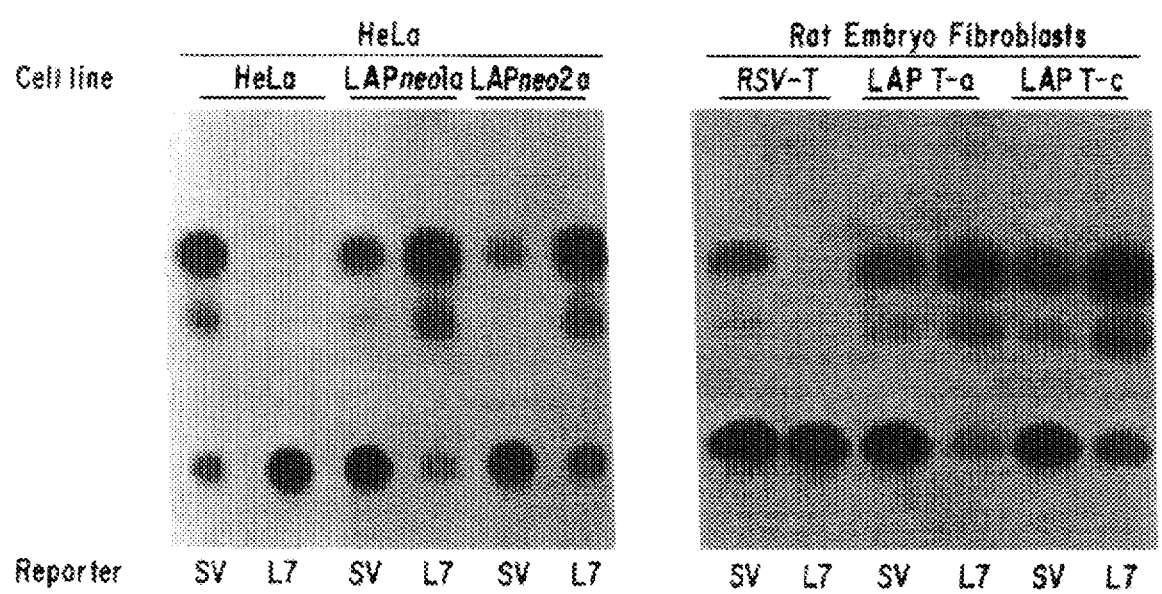

[a]The indicated cells were transfected with 1 μg of the marker gene alone (-) or with 1 μg of pHβLAP348 and calf thymus DNA for a total of 25 μg of DNA. The number of G418$^r$ colonies and transformed foci were determined by visually scanning the plates before and after fixation and staining with formaldehyde and cresyl violet.
[b]Cell lines were cloned and determined to be LAP + by their ability to support high levels of expression of pL7CAT as shown in FIG. 7C. The expression of LAP348 protein was verified by immunofluorescence/immunoprecipitation analysis (see FIG. 7B).

Transfection of pL1-3neo into HeLa cells or pL2T-antigen into REF cells resulted in very few G418$^r$ colonies or transformed foci, respectively; however, cotransfection with pHβA348 resulted in production of significantly higher numbers of G418$^r$ colonies and transformed foci. No effects on colony number were observed after cotransfection with lac repressor constructs indicating that the activation function of LAP was required for this enhancement. These data demonstrated a strong selection for LAP348 expression in the HeLa cell and REF cell assays.

No enhancement of colony formation was seen in mouse Ltk cells. In fact, cotransfection of pHβA348 lowered the number of G418$^r$ Ltk colonies. These data suggest that pL1-3neo is sufficient in Ltk cells for transformation without transactivation. The decrease in colony number may indicate some toxicity of the LAP construct in Ltk cells. Thus, transformation assays in some cell lines may require alternative basal promoters for the chosen selectable marker and test genes.

G418$^r$ colonies and transformed foci resulting after cotransfection with the LAP vector were isolated, propagated and screened for the presence of LAP activity. A cell line was judged to be LAP$^+$ if it supported high levels of CAT expression from a supertransfected LAP-inducible CAT gene such as pL7CAT (Table I and FIG. 7C). The presence of LAP in the cells was also verified in most cases by immunoprecipitation and immunofluorescence (FIG. 7B). All of the HeLa lines and REF lines (6 out of 6) expressed LAP activity (Table I); however, only 1 out of 7 G418$^r$ Ltk- lines expressed LAP. FIG. 7B shows the fluorescent micrographs of two representative LAP+ HeLa lines (LAPneo2b and LAPneo6b cells) stained using anti-lac repressor antiserum as described above. Virtually all of the cells showed distinct nuclear fluorescence indicating that LAP348 was efficiently sequestered in the nucleus. FIG. 7C illustrates the CAT activity produced following transfection of several representative LAP$^+$ cell lines with pL7CAT or pSV2CAT. pL7CAT was expressed at low levels in control HeLa cells or MSV-T cells, an REF cell line transformed with T-antigen under control of the murine sarcoma virus long terminal repeat. The LAP$^+$ cell lines, however, expressed pL7CAT at greatly enhanced levels (5–10 fold greater than with pSV2CAT comparable to that observed in cotransfection assays. Preliminary experiments indicate that reporters such as pL14CAT and pL21CAT are expressed greater than 30-fold more efficiently than pSV2CAT in LAP+ cell lines. Thus, high levels of LAP-inducible expression by operator-containing promoters did not require high amounts of LAP that might be produced in the transient assays.

One Ltk- line (L3) stably expressing LAP activity was identified even though selection assays did not suggest a requirement for LAP for G418$^r$. The isolation of this line may be fortuitous or may indicate that some transformants require LAP for expression of the neo gene. In either case, it should be noted that this and the other LAP+ lines have stably produced LAP348 over 3 months of continuous passage indicating little selection against LAP expression.

Experiments were also carried out to determine if the LAP activity in the stable cell lines was regulatable by IPTG HeLa cells or LAPneo2b cells were transfected with either pSV2CAT or pL1-2CAT, with or without IPTG in the medium (FIG. 8). pL1-2CAT was efficiently expressed in LAPneo2b cells, but not in HeLa cells (lanes 3 and 7). Addition of IPTG to the medium two days before transfection reduced expression of pL1-2CAT greater than 30-fold (lane 8) without significantly affecting expression of pSV2CAT (lanes 2 and 6). Similar results were observed in all other LAP$^+$ cell lines tested.

6.3. Discussion

The experiments detail the development of a novel regulatory system for vertebrate cells. Central to this system is the conversion of the lac repressor into a transcriptional transactivator (LAP). The LAP retains the ability to specifically bind operator DNA and to be allosterically regulated by IPTG even though both the very 5' end and the 3' end of the gene have been modified. These results are consistent with the observation from lacI/lacZ and lacI/T7 endonuclease fusions that the very carboxyl terminus of lac repressor can be modified and still retain specific DNA binding activity (Muller-Hill and Kania 1974, Nature 249:561–563; Panayotatos et al. 1989, J. Biol. Chem. 264:15066–15069). The LAPs, however, were designed such that the carboxyl terminus was left intact in case it was required for tetramerization. Although LAP348 has not been tested for tetramerization, the synergistic effect of spaced operators on transactivation by LAP (FIGS. 2B and 3) suggests that tetramers of LAP may be binding separated operators.

Although the actual affinities of LAPs for operator DNA have not been measured, the complex between LAP and operator DNA in mammalian cells must be quite stable since LAP348 was also able to block expression of an SV40 promoter containing an operator downstream from the transcriptional start site even if the promoter also contained an upstream, activating operator (FIG. 5). One or two tandem operations allowed for activation by LAP and multiple spaced operators acted synergistically (FIG. 3). Similarly, many other eukaryotic transactivators appear to require multiple sites for efficient activation and appear to interact synergistically.

Although multiple glucocorticoid response elements or metal response elements have additive effects on transcription (Searle et al. 1985, Mol. Cell Biol. 5:1490–1489; Toohey et al. 1986, Mol. Cell Biol. 6:4526–4538; Strahle et al. 1988, EMBO 11:3389–3395), at least two response elements are required for efficient induction. Further, there is a synergistic effect between single glucocorticoid or estrogen response elements and other transcription factor binding sites.

Synergistic effects on activation by LAP were only observed when tandem operators be separated by some distance. Promoters containing two operators separated by about 100 base pairs (pL1-1CAT) produced approximately five to ten times more CAT activity than promoters containing one or two tandem operators (FIG. 3). Also, little difference was observed between promoters containing 2 or 4 spaced operators (pL1-1CAT and pL1-3CAT), whereas a promoter containing 7 operators consisting of two spaced arrays (pL7CAT), consisting of the two spaced operator arrays A and B, produced about twice the CAT activity expected for an additive affect of the operators. Multimerizing the pL7 operators, however, in pL14CAT and pL21CAT displayed an additive effect, respectively, doubling and tripling the amount of CAT produced by pL7CAT.

These data are consistent with studies showing that spaced operators greatly enhance the ability of the lac repressor to repress transcription in *E. coli* (Besse et al. 1986, EMBO 5:1377–1381; Mossing and Record 1986 Science 233:889–892). Indeed, the affinity of lac repressor for tandem operators has been shown to increase as the distance between operators is increased (Mossing and Record 1986, Science 233:889–892). This relationship between spacing length and affinity parallels a relationship between length and the ability of the DNA to form a circle. The increase in repressor affinity was suggested to be related to the ability to form stable loops of DNA. Supporting this is the observation that a receptor tetramer bound to spatially separated operators can loop out intervening DNA in a length-dependent fashion (Kramer et al. 1987, EMBO 6:1481–1491).

The LAPs offer several advantages for use as an inducible expression system in vertebrate cells. First, LAP inducible promoters can be activated to very high levels. Vectors such as pL7CAT and pL14CAT and pL21CAT were induced over 1000-fold in response to LAP, producing 10–30 times as much CAT as pSV2CAT either in transient cotransfections or in transfections into stable, LAP+ cell lines (FIGS. 3 and 7). Thus, the LAP system has the potential to regulate transcription over three orders of magnitude reaching levels comparable to bacterial regulatory systems. This is in contrast to cell lines expressing the lac repressor which typically display induced levels of expression lower than that for the parent promoters (Brown et al., 1987, Cell 49:603–612; Hu and Davidson, 1987, Cell 48:555–566). This observation has been attributed to the inability of IPTG to completely relieve repression and that insertion of operators around the start site of transcription appears to lower the basal expression of the promoter. An additional disadvantage in the use of lacI as a repressor is that cell lines must produce large amounts of repressor to saturate the operator and block expression. The addition of a nuclear localization signal also concentrates lac repressor and LAP in the nucleus and should lower the amount of protein needed to affect regulation.

Second, the LAP system is highly specific. The lac operator is a complex 25 base pair sequence which appears extremely infrequently in vertebrate genomes. Further, the observation that multiple spaced operators are required for efficient activation suggests that virtually no cellular genes would be significantly affected by LAP expression. In contrast, heat shock, heavy metal or hormone induction of promoters is likely to alter expression of a variety of genes. This specificity makes LAP an ideal transactivator for use in transgenic animals.

Third, LAP retains the ability to act as a repressor (FIG. 5). Thus, LAP may be used as a bidirectional switch to turn off one gene while turning on another. However, it should be noted that our experiments to date indicate that LAP is not as efficient a repressor as lacI5'N1. The reason for this is unclear and the utility of LAP as a repressor must be further examined.

Fourth, LAP is allosterically regulated by IPTG (FIGS. 6 and 8). IPTG in the medium inhibited LAP activity both in transient assays and in stable cell lines. Experiments have also demonstrated that expression from the integrated LAP-inducible neo and T-antigen genes described in FIG. 7 are highly regulatable by IPTG in transformed cell lines and that the transformed phenotype of the pL2T-antigen transformed cells can be largely reversed by IPTG. Thus, IPTG provides a useful switch for regulating LAP-inducible genes in stable cell lines. As pointed out by others, however, IPTG induction in mammalian cells is slow and occurs over hours or days as compared with minutes in bacteria; indeed, IPTG never completely eliminated activation by LAP in these studies. In addition, preliminary experiments indicate that regulation by IPTG is less efficient for the pL14 and pL21 promoters in transient transfection assays compared with that for the pL1-2 or pL7 promoters. Yet another advantage to the LAP system is the ability to easily select for LAP+ cell lines using LAP inducible markers (FIG. 7 and Table I). These selections should not only be useful in generating and maintaining LAP+ lines, but should be useful as phenotypic tags to coselect or identify cells also expressing test genes under the regulation of LAP.

7. EXAMPLE: CONSTRUCTION OF TEMPERATURE-SENSITIVE LAP267 TRANSACTIVATING PROTEIN

LAP267 was constructed as described for LAP348 in Section 6.1.1., supra, except that the VP16 segment was inserted at an EcoRV site after amino acid 267 in the lacI coding region (FIG. 1A). The LAP267 transactivating protein was observed to have several characteristics which make it especially attractive for control of transcription in animal cells.

First, transactivator function of LAP267 was found to be temperature-sensitive. As shown in Table II, the ability of LAP267 to enhance the expression of CAT reporter gene from the pL7CAT construct (FIG. 3) was temperature-dependent. HeLa cells were co-transfected with either LAP267, LAP348 (as a positive control), or pBR322 (as a negative control). Table II presents CAT activity as the percent of input $^{14}$C-chloramphenicol that was acetylated,

TABLE II

Transcriptional Activation by LAP267 is temperature sensitive

| Activator | CAT Activity | |
|---|---|---|
| | 32° C. | 39.5° C. |
| pBR322 | <0.1 | 0.26 |
| LAP267 | 36. | 0.41 |
| LAP348 | 68. | >90. | and indicates that LAP267 was virtually nonfunctional at 39.5° C., but active at 32° C. HeLa cells were cotransfected with plasmids encoding the LAP267 or LAP348 activator protein and pL14CAT, encoding CAT reporter gene. CAT expression was then monitored as a function of IPTG concentration at 39.5° C., and the "reverse regulator" effect of IPTG on LAP267 was observed (FIG. 9). This property enables the expression of genes controlled by LAP267 to be induced at 39.5° C. by addition of IPTG to the culture medium.

8. DEPOSIT OF MICROORGANISMS

The following plasmids have been deposited with the Northern Regional Research Center (NRRL):

| Plasmed | Host | Accession Number |
|---|---|---|
| pHCMVLAP348 | E. coli | NRRLB-18664 |
| pHCMVLAP267 | E. coli | NRRLB-186673 |

The present invention is not to be limited in scope by the genes and proteins exemplified or deposited microorganisms which are intended as but single illustrations of one aspect of the invention. Indeed, various modifications of the invention in addition to those shown and described herein will become apparent to those skilled in the art from the foregoing description and accompanying figures. Such modifications are intended to fall within the scope of the appended claims.

Various publications have been cited herein; these publications are incorporated by reference in their entirety.

What is claimed is:

1. A recombinant nucleic acid molecule encoding a chimeric transactivator comprising:

(i) a DNA binding domain of a DNA binding protein wherein said DNA binding protein is the bacterial lac I protein, and (ii) a functional transcriptional activator domain of a vertebrate transcriptional activator protein, wherein said transcriptional activator protein is VP16 of *Herpes simplex* virus.

2. The recombinant nucleic acid molecule of claim 1 in which nucleic acids encoding about amino acids 369 to 488 of VP16 are inserted at about the codon for lac I amino acid 348.

3. A plasmid pHCMVLAP348, deposited with the Northern Regional Research Center and having accession number NRRL B-18664.

4. The recombinant nucleic acid molecule of claim 1 in which nucleic acids encoding about amino acids 369 to 488 of VP16 are inserted at about the codon for lac I amino acid 267.

5. A plasmid pHCMVLAP267, deposited with the Northern Regional Research Center and having accession number NRRL B-18663.

6. The recombinant nucleic acid molecule of claim 1, which comprises a nucleic acid sequence encoding a nuclear localization signal.

7. A cell line comprising the recombinant nucleic acid molecule of claim 1.

8. A cell line comprising the recombinant nucleic acid molecule of claim 2.

9. A cell line comprising the plasmid of claim 3.

10. A cell line comprising the recombinant nucleic acid molecule of claim 4.

11. A cell line comprising the plasmid of claim 5.

* * * * *